US008148601B2

(12) United States Patent
Fukuoka et al.

(10) Patent No.: US 8,148,601 B2
(45) Date of Patent: Apr. 3, 2012

(54) RICE BLAST SUSCEPTIBILITY GENE PI21, RESISTANCE GENE PI21, AND USES THEREOF

(75) Inventors: Shuichi Fukuoka, Ibaraki (JP); Kazutoshi Okuno, Ibaraki (JP); Makoto Kawase, Ibaraki (JP)

(73) Assignee: National Institute of Agrobiological Sciences, Tsukuba-shi, Ibaraki (JP)

( * ) Notice: Subject to any disclaimer, the term of this patent is extended or adjusted under 35 U.S.C. 154(b) by 0 days.

(21) Appl. No.: 12/881,685

(22) Filed: Sep. 14, 2010

(65) Prior Publication Data

US 2011/0083233 A1    Apr. 7, 2011

Related U.S. Application Data

(62) Division of application No. 11/922,994, filed as application No. PCT/JP2006/311341 on Jun. 6, 2006.

(30) Foreign Application Priority Data

Jun. 28, 2005   (JP) ................................ 2005-187867

(51) Int. Cl.
*A01H 1/00* (2006.01)
*A01H 5/00* (2006.01)
*C12Q 1/68* (2006.01)

(52) U.S. Cl. ........ 800/265; 800/260; 800/266; 800/267; 800/298; 435/6.1

(58) Field of Classification Search ........................ None
See application file for complete search history.

(56) References Cited

U.S. PATENT DOCUMENTS

| 6,124,126 A | 9/2000 | Ito et al. |
| 6,963,020 B1 * | 11/2005 | Okuno et al. ................. 800/267 |
| 2002/0108140 A1 | 8/2002 | Bennetzen |
| 2004/0123343 A1 | 6/2004 | La Rosa et al. |
| 2006/0123505 A1 | 6/2006 | Kikuchi et al. |

FOREIGN PATENT DOCUMENTS

| JP | 2000-93028 | 4/2000 |
| JP | 2000-342262 | 12/2000 |
| JP | 3376453 | 12/2002 |
| JP | 2003-88379 | 3/2003 |
| JP | 2003-199448 | 7/2003 |
| JP | 2003-199577 | 7/2003 |
| JP | 2004-329215 | 11/2004 |
| JP | 2005-185101 | 7/2005 |

OTHER PUBLICATIONS

Bryan, Gregory T. et al., "A Single Amino Acid Difference Distinguishes Resistant and Susceptible Alleles of the Rice Blast Resistance Gene Pi-ta," The Plant Cell, vol. 12:2033-2045 (2000).
Feng, Qi et al., "Sequence and analysis of rice chromosome 4," Nature, vol. 420:316-320 (2002).
Fukuoka, Shuichi et al., "Genetic Dissection and Mapping of Genes Conferring Field Resistance to Rice Blast in Japanese Upland Rice," Rice Blast: Interaction wtih Rice and Control, Proceedings of the 3rd International Rice Blast Conference, Kluwer Academic Publishers, Shinji Kawasaki, Ed., pp. 131-136 (2004).
Fukuoka, S. et al., "Loss of function of a proline-containing protein confers durable disease resistance in rice," Science, vol. 325(5943):998-1001 (2009).
Fukuoka, Shuichi et al., "Natural Variationation and the Study for Enhancing Genetic Diversity in Rice," Gamma Field Symposium, No. 44, Genome and Post-Genome Researches in Crops and Mutation, pp. 45-53 (2005).
Fukuoka, S. et al., "Nippon Rikuto Hinshu no Imochibyo Hojo Teikosei o Shihai suru Idenshi pi21(t)," Breeding Research, vol. 1:255 (1999).
Fukuoka, Shuichi et al., "Nippon Rikuto Hinshu no Imochibyo Hojo Teikosei ni Kanyo suru QTL no Kenshutsu," Seibutsu Shigen Kenkyu Seika Joho., vol. 7:5-6 (1998).
Fukuoka, S. et al., "QTL analysis and mapping of pi21, a recessive gene for field resistance to rice blast in Japanese upland rice," Theor. Appl. Genet., vol. 103:185-190 (2001).
GENBANK Accession No. AK070581, Kikuchi, S., "Rice full-length cDNS," Jul. 18, 2003.
GENBANK Accession No. AL731642, Feng, Q. et al., "Sequence and analysis of rice chromosome 4," Nature, vol. 420(6913):316-320 (2002) Apr. 16, 2005.
GENBANK Accession No. CAE05282, Feng, Q. et al., "Sequence and analysis of rice chromosome 4," Nature, vol. 420(6913):316-320 (2002) Apr. 16, 2005.
Kiyosawa, S. et al., "Blast Disease Resistance and Inheritance of Resistance in Rice Cultivars," Rice Blast and Breeding for its Resistance, Kouzaka and Yamasaki eds., Hakuyusha publisher, pp. 175-186 (1980).
Miyamoto, Masaru et al., "Mapping of Quantitative Trait Loci Conferring Blast Field Resistance in the Japanese Upland Rice Variety Kahei," Beeding Science, vol. 51:257-261 (2001).
Miyamoto, Masaru et al., "Relationship Between RFLP Loci with Different Alleles on Chromosome 4 and the Levels of Blast Field Resistance in Japanese Upland Rice Varieties," Breeding Science, vol. 53:1-5 (2003).
Saka, Norikuni et al., "Evaluating near-isogenic lines with QTLs for field resistance to rice blast from upland rice cultivar Sensho through marker-aided selection," Rice is Life: Scientific Perspectives for the 21st Century, pp. 487-489 (2005).

(Continued)

*Primary Examiner* — Medina A Ibrahim
(74) *Attorney, Agent, or Firm* — Nelson Mullins Riley & Scarborough LLP; Jeanne M. DiGiorgio, Esq.; Erika L. Lawson

(57) ABSTRACT

The present inventors succeeded in isolating the rice field resistance gene pi21 by linkage analysis, and found that field resistance to blast in plants could be modified by introducing or controlling the expression of the gene. Thus, it became possible to efficiently confer plants with field resistance. It also became possible to select, at an early stage, rice plants having field resistance to blast. Moreover, by changing the tissue specificity of expression and the expression level of the gene involved in field resistance, varieties having resistance as well as high practical use can be grown.

14 Claims, 4 Drawing Sheets

OTHER PUBLICATIONS

Wang, Guo-Liang et al., "RFLP Mapping of Genes Conferring Complete and Partial Resistance to Blast in a Durably Resistant Rice Cultivar," Genetics, vol. 136:1421-1434 (1994).

Wang, Zi-Xuan et al., "The Pib gene for rice blast resistance belongs to the nucleotide binding and leucine-rich repeat class of plant disease resistance genes," The Plant Journal, vol. 19(1):55-64 (1999).

International Search Report for Application No. PCT/JP2006/311341, dated Jul. 11, 2006.

Supplementary European Search Report for Application No. 06757079.6, dated Jan. 19, 2009.

Parker, Jane E. et al., "Characterization of eds1, a Mutation in *Arabidopsis* Suppressing Resistance to *Peronospora parasitica* Specified by Several Different RPP Genes," The Plant Cell, vol. 8:2033-2046 (1996).

International Preliminary Report on Patentability for Application No. PCT/JP2006/311341, dated Jan. 9, 2008.

* cited by examiner

AA-pi21
(RESISTANT)

*AICHI ASAHI*
(SUSCEPTIBLE)

A. VECTOR ALONE (0)

B. 1 COPY (1)

C. MULTIPLE COPIES (3≦)

SEQUENCE LISTING

<160> NUMBER OF SEQ ID NOS: 27

<210> SEQ ID NO 1
<211> LENGTH: 4817
<212> TYPE: DNA
<213> ORGANISM: Oryza sativa

<400> SEQUENCE: 1

```
ctagatgatg ctttatgtga aggcaataaa tgataattaa gtgtaatata atgtattttt    60
taaacatcgt agtgaagtcc catttctagt acgtaatgga tcgaaatggg gagggactgc   120
ttctctttta gaaaaaaaaa atgtaaaatt gagatgagct tttataagac atgtaaggcc   180
atatgtctag tgtaagtatg atgctagcaa gcacatttta gcatcttaaa ataaaaagca   240
agcacattaa tattttagga gttagcatgg atgcaataca gtagaagagg agatgccaac   300
aaaaagaat atggaaaatt tgtttcatac catcaaaagt tcctgtgttt tgctttatac   360
catcagcgtt tgtggtgtac tttaacacca tccaaagttt gctccgttac ctatctactc   420
cacgaaatgt gcttgctagc atggatgaaa agtaaccga aacaaacagt tgtggtatac   480
tcctaagtaa tcctaagtag ccaccggatt caatacttta ttctcaatcg tccttctagt   540
ctattcccaa ttatatgggt ttgacccgtt acaacgtacg gacatgttac tagcgtaagg   600
aaagagatgg tttctgaaag agttttttt ttccaacagt cctacccaat ctatagcgct   660
agacaagaaa gcgaaagcta aacccatatt tattaccgta atgttgcaaa cttaatatta   720
cctgcaatag acatgcccta acatggtttc aggaccacaa accagagctc taaaattccg   780
agcacatgtt cagaatatat atacattttt aattcccttc tatactactc caacttacct   840
ctatggaggt aagaggctaa aattgaaact agataactga atgttcttat attttttccta   900
ataaaaatat aattgctcct ttcatttaat acttatatca caacatgtag ccatatgagc   960
caaaactgta ttagccatat tttagcgaat aaggctcaat gcgattctgt gtctgagctc  1020
tggcctgaaa attcttgtaa ctttatctca catatggtgt gtgaggaagc ttctcatgag  1080
taatatattc cctatttccc cgcaaaaaaa aaaacttata tcacaacaaa aatggaaaag  1140
accaacactg agtattgtag aagctagtac ttttggcaaa tgtgcccgaa gatccccaaa  1200
acagtttgtg gcataattca gaagattgtt agctcagaaa tcatttcaga ctaggatatt  1260
gccgacacat cagagttctc gtgtaatcac gaagcaagga actgtacagt gcagtgatga  1320
tatacaacta taggagagga cgaactgata ctgacggatg ctgtgtgtaa aatatctctg  1380
taaaatcagg aatactggga gactgattgg atgataggtt tatacggtca caatcatctc  1440
gttaaacaca cttttcatta aagaggaatt accaaataca gtaattgatt cgacggtgcc  1500
gcgagaaatg tgctatatat aaatgctcac ctatatttgg gcagattagt taatttcagg  1560
aattttccac agagaaagct aaatgagtgc taaatgagtc gcattgcgta ctactacaag  1620
ggtccaaaca gaaattgata tctgaaatta gcttttctta agataacaat gatatttttt  1680
tttattgaag cacaaggtgt gcctgaaatc gaattctgaa aggtattctt attttttcaga  1740
ggaaaatgta cagtggtacc attctgaaag ctaattgaga gatgacaagg cgtgagaagg  1800
accaaactgt cctatataca tgtggtcatt ttccatctct tgcaataggt tatcaagacc  1860
cctcctgaaa catggaccgt ccagatgcga tccgacggac gaaaaaaacc aatggcagaa  1920
tatttcaggc tctggcatat ccaaacataa ataagtaaca taaggttcag ctctgctcca  1980
tccatgcatc gcctccatta ttcatgcttc gattctccat gctttcctct actgctcatt  2040
ggtaacattc ggcaaatttg acaggtgagc tcagtatttt aaatcttaat gtagtacttt  2100
ggtgtgctaa tctttgctct gttcaaaaga gaattctggt ttctttgcta ttttgaaaag  2160
agaattttcg ttacaggact tcaacttcca taatactttt ttttataatt aaggcatgat  2220
atatatcttc tttctgaatt ccacgggaat tgcacttttt cctgagaaat ttgtaaagag  2280
catgcctgtt aattgcaagg ggcccctaac tctgttatga gaaaagagaa ctatataaga  2340
```

```
tgctcaataa gcacctcttt ttttttttct gttaactgac caaagcctgt ctatctgcat    2400
ttttttttgt tttttgtttt tcttgtgtgc agatgggtat attggtcatc ttggtggacc    2460
tgcaatgctg ccgctgcgat gccaagatca ggaaggtcct gggctgcctt gaaggtataa    2520
taaattctgc ccgaatcgtc catgtttgat tgaattttca aggctaatca gcagtgttcc    2580
tgctcaattg ggagcaaaac ctctgttaaa aagggtgtgt ttgaatgaat ataattgaat    2640
atgaacgcag aggagtactg catcgagaag gtggagtacg acgtgaagaa caacagggtg    2700
atcgtgcgcg ggaagttcga cccggagaag ctgtgcaaga agatctggtg caaggccggc    2760
aagatcatca aggagatcct catcgtcgac gtctggccgc cgccgctgcc gcagccgccg    2820
ccgccgtgca agccgccgcc gtgcgagaag cctccggagg actgcaagcc caagccctgc    2880
cattgctgca gctgcgagaa gcccaagccc aagcccaagc cctgccactg cgagaagccc    2940
aagccctgtc actgcgagaa gcccaagcca tgcgagaagc cgccgccgtg caagccggag    3000
gagccgccga gccgccgcc ggagaagccg ccgccgaagc cggagtgcaa gctggtgccg    3060
tacccttacc cggtgccgta cccgtacgcc gggcagtggt gctgcccaaa gcctgagccg    3120
ccgaagccgc cgccggagcc accgaaggag ccggagccgc cgaagccgtg cgggtgctcg    3180
cacgccttcg tgtgcgtctg caagccggcg ccgccgccgc cgccgccgtg cgggtgctcg    3240
gggggccacg ggaactgcgg ctgcggcatc aggccgtggc cgccgcaggt gtggccgccg    3300
ccgcccgtct gcccgccgcc gccgtggtgc tacaccgagg acaacgccaa cgcctgctcc    3360
atcatgtgat ggccggccgg cggtcggcgt cgatcacgat catctctgct gcttaatttc    3420
cttgcttgct actacctctg ctcctttcct tgcctcggaa atcggaataa attaaacacg    3480
aggctgatcg atgtgtttgt aattaatcca tggtgtttgt gttgtgtgct gtgtgggctg    3540
tataataatt aattacagta tgttcatgta aatttgtttg tttgtttgtt tatgttgttc    3600
gatatgtata attatgtaca ataattaatc gtggagaggc tcactaaact cataaactgt    3660
agagtatctt ggctgtaaaa gtgtggcaat ttatctttt cttgtgttag cattggctac    3720
aaatagtttt tggccgtctt ttctcttcgt ttctccccttt ctttatgaga ttaattgtgt    3780
gctgacctag atcaaattat agcgcgctga cctagttttta ttgtaactgc tcttatggat    3840
gtctgctaac accatcaaac atgattaccg tggtatattt gtcttaatta ctactaacta    3900
ggactaccta ggggcacccct tgcatatgtt ttttttcga acgaccagat agatttgagt    3960
catttgacta gcgttatatt aataggaggg aaaaaaaata caaagtacaa atatccaaca    4020
ggccgagaaa agagaaaaaa aactgtacat gcctacgtgc aaacaagatt gcacgaagct    4080
ctcctcactc ctcatggcaa cattctccca atgtgtttag catcgaaaat accccaccaa    4140
cctcgtcttg gatgtgactg gtcatttggt gtattgtcgc ctccttttcc ctctgaagat    4200
tcttacgttc cattccttcc aaatttccta ggcgatgagc aagaaaagag atctgagccc    4260
ttttgtttta gttacttcca agtcgcttgt tccttgtgtc caccaatgca agaggtttct    4320
actgtcattc catttcagaa taagccaatt gagaactcca accagatttt acttcgaaac    4380
caggcattcg aacataaggt ggtcgacaat gtcgagattc cggattagca gagttatttg    4440
gtttgagagt cacattccta caaccaatag aaaaccatcc tatggaccat ttagatagtg    4500
tcctagtatt tgcttttata tttgctataa atattcttcc tttattgttt ttggagttca    4560
caaacttaat aatcaaactt tgtgattttt taatttccat taacgaattc aaggaaccac    4620
ctttatctct catcttcatt gcacactact gatttctttc atccttaggg acatatggtt    4680
gatacggaga ctgttttctt atcattatct aaaaaaaatc taagggggcat atatatattg    4740
```

```
tgtttctctct cattcatgca tttcgcactt ttccctattc gtgaaatacc atttcccaca    4800
tgagtgcaat gtttcctt                                                   4817

<210> SEQ ID NO 2
<211> LENGTH: 801
<212> TYPE: DNA
<213> ORGANISM: Oryza sativa

<400> SEQUENCE: 2
atgggtatat tggtcatctt ggtggacctg caatgctgcc gctgcgatgc caagatcagg      60
aaggtcctgg gctgccttga agaggagtac tgcatcgaga aggtggagta cgacgtgaag     120
aacaacaggg tgatcgtgcg cgggaagttc gacccggaga agctgtgcaa gagatctgg      180 tgcaaggccg gcaagatcat caaggagatc ctcatcgtcg acgtctggcc gccgccgctg     240
ccgcagccgc cgccgccgtg caagccgccg ccgtgcgaga gcctccgga ggactgcaag      300 cccaagccct gccattgctg cagctgcgag aagcccaagc ccaagcccaa gccctgccac     360
tgcgagaagc ccaagccctg tcactgcgag aagcccaagc catgcgagaa gccgccgccg     420
tgcaagccgg aggagccgcc gaagccgccg ccggagaagc cgccgccgaa gccggagtgc     480
aagctggtgc cgtaccctta cccggtgccg tacccgtacg ccgggcagtg gtgctgccca     540
aagcctgagc cgccgaagcc gccgccggag ccaccgaagg agccggagcc gccgaagccg     600
tgcgggtgct cgcacgcctt cgtgtgcgtc tgcaagccgg cgccgccgcc gccgccgccg     660
tgcgggtgct cggggggcca cgggaactgc ggctgcggca tcaggccgtg gccgccgcag     720
gtgtggccgc cgccgcccgt ctgcccgccg ccgccgtggt gctacaccga ggacaacgcc     780
aacgcctgct ccatcatgtg a                                                801

<210> SEQ ID NO 3
<211> LENGTH: 266
<212> TYPE: PRT
<213> ORGANISM: Oryza sativa

<400> SEQUENCE: 3

Met Gly Ile Leu Val Ile Leu Val Asp Leu Gln Cys Cys Arg Cys Asp
1               5                   10                  15

Ala Lys Ile Arg Lys Val Leu Gly Cys Leu Glu Glu Glu Tyr Cys Ile
            20                  25                  30

Glu Lys Val Glu Tyr Asp Val Lys Asn Asn Arg Val Ile Val Arg Gly
        35                  40                  45

Lys Phe Asp Pro Glu Lys Leu Cys Lys Lys Ile Trp Cys Lys Ala Gly
    50                  55                  60

Lys Ile Ile Lys Glu Ile Leu Ile Val Asp Val Trp Pro Pro Pro Leu
65                  70                  75                  80

Pro Gln Pro Pro Pro Pro Cys Lys Pro Pro Pro Cys Glu Lys Pro Pro
                85                  90                  95

Glu Asp Cys Lys Pro Lys Pro Cys His Cys Cys Ser Cys Glu Lys Pro
            100                 105                 110

Lys Pro Lys Pro Lys Pro Cys His Cys Glu Lys Pro Lys Pro Cys His
        115                 120                 125

Cys Glu Lys Pro Lys Pro Cys Glu Lys Pro Pro Cys Lys Pro Glu
    130                 135                 140

Glu Pro Pro Lys Pro Pro Glu Lys Pro Pro Lys Pro Glu Cys
145                 150                 155                 160

Lys Leu Val Pro Tyr Pro Tyr Pro Val Pro Tyr Pro Tyr Ala Gly Gln
                165                 170                 175
```

```
Trp Cys Cys Pro Lys Pro Glu Pro Lys Pro Pro Glu Pro Pro
            180                 185                 190
Lys Glu Pro Glu Pro Pro Lys Pro Cys Gly Cys Ser His Ala Phe Val
            195                 200                 205
Cys Val Cys Lys Pro Ala Pro Pro Pro Pro Pro Cys Gly Cys Ser
        210                 215                 220
Gly Gly His Gly Asn Cys Gly Cys Gly Ile Arg Pro Trp Pro Pro Gln
225             230                 235                 240
Val Trp Pro Pro Pro Val Cys Pro Pro Pro Trp Cys Tyr Thr
                245                 250                 255
Glu Asp Asn Ala Asn Ala Cys Ser Ile Met
            260                 265

<210> SEQ ID NO 4
<211> LENGTH: 4745
<212> TYPE: DNA
<213> ORGANISM: Oryza sativa

<400> SEQUENCE: 4
ctagatgatg ctttatgtga aggcaataaa tgataattaa gtgtaatata atgtattttt      60
taaacatcgt agtgaagtcc catttctagt acgtaatgga tcgaaatggg gagggactgc     120
ttctctttta gaaaaaaaat gtaaaattga gatgagcttt tataagacat gtaaggccat     180
atgtctagtg taagtatgat gctagcaagc acattttagc atcttaaaat aaaaagcaag     240
cacattaata tttaggagt tagcatggat gcaatacagt agaagaggag atgccaacaa      300 aaagaatat ggaaaatttg tttcatacca tcaaaagttc ctgtgttttg ctttatacca     360
tcagcgtttg tggtgtactt taacaccatc caaagtttgc tccgttacct atctactcca     420
cgaaatgtgc ttgctagcat ggatgaaaaa gtaaccgaaa caaacagttg tggtatactc     480
ctaagtaatc ctaagtagcc accggattca atactttatt ctcaatcgtc cttctagtct     540
attcccaatt atatgggttt gacccgttac aacgtacgga catgttacta gcgtaaggaa     600
agagatggtt tctgaaagag ttttttttt ccaacagtcc tacccaatct atagcgctag      660
acaagaaagc gaaagctaaa cccatatttta ttaccgtaat gttgcaaact taatattacc    720
tgcaatagac atgccctaac atggtttcag gaccacaaac cagagctcta aaattccgag    780
cacatgttca gaatatatat acattttaa ttcccttcta tactactcca acttacctct      840
atggaggtaa gaggctaaaa ttgaaactag ataactgaat gttcttatat ttttcctaat     900
aaaaatataa ttgctccttt catttaatac ttatatcaca acatgtagcc atatgagcca     960
aaactgtatt agccatattt tagcgaataa ggctcaatgc gattctgtgt ctgagctctg    1020
gcctgaaaat tcttgtaact ttatctcaca tatggtgtgt gaggaagctt ctcatgagta    1080
atatattccc tatttccccg caaaaaaaaa aactatatc acaacaaaaa tggaaaagac     1140
caacactgag tattgtagaa gctagtactt ttggcaaatg tgcccgaaga tcccaaaaac    1200
agtttgtggc ataattcaga agattgttag ctcagaaatc atttcagact aggatattgc    1260
cgacacatca gagttctcgt gtaatcacga agcaaggaac tgtacagtgc agtgatgata    1320
tacaactata ggagaggacg aactgatact gacggatgct gtgtgtaaaa tatctctgta    1380
aaatcaggaa tactgggaga ctgattggat gataggttta tacggtcaca atcatctcgt    1440
taaacacact tttcattaaa gaggaattac caaatacagt aattgattcg acggtgccgc    1500
gagaaatgtg ctatatataa atgctcacct atatttgggc agattagtta atttcaggaa    1560
ttttccacag agaaagctaa atgagtgcta aatgagtcgc attgcgtact actacaaggg    1620
```

```
tccaaacaga aattgatatc tgaaattagc ttttcttaag ataacaatga tatttttttt   1680
tattgaagca caaggtgtgc ctgaaatcga attctgaaag gtattcttat ttttcagagg   1740
aaaatgtaca gtggtaccat tctgaaagct aattgagaga tgacaaggcg tgagaaggac   1800
caaactgtcc tatatacatg tggtcatttt ccatctcttg caataggtta tcaagacccc   1860
tcctgaaaca tggaccgtcc agatgcgatc cgacggacga aaaaaaccaa tggcagaata   1920
tttcaggctc tggcatatcc aaacataaat aagtaacata aggttcagct ctgctccatc   1980
catgcatcgc ctccattatt catgcttcga ttctccatgc tttcctctac tgctcattgg   2040
taacattcgg caaatttgac aggtgagctc agtattttaa atcttaatgt agtactttgg   2100
tgtgctaatc tttgctctgt tcaaaagaga attctggttt ctttgctatt ttgaaaagag   2160
aattttcgtt acaggacttc aacttccata atactttttt ttataattaa ggcatgatat   2220
atatcttctt tctgaattcc acgggaattg cacttttttcc tgagaaattt gtaaagagca   2280
tgcctgttaa ttgcaagggg cccctaactc tgttatgaga aaagagaact atataagatg   2340
ctcaataagc acctcttttt tttttttctgt taactgacca aagcctgtct atctgcattt   2400
ttttttgttt tttgttttttc ttgtgtgcag atgggtatat tggtcatctt ggtgaacctg   2460
caatgctgcc gctgcgatgc caagatcagg aaggtcctgg gctgccttga aggtataata   2520
aattctgccc gaatcgtcca tgtttgattg aattttcaag gctaatcagc agtgttcctg   2580
ctcaattggg agcaaaacct ctgttaaaaa gggtgtgttt gaatgaatat aattgaatat   2640
gaacgcagag gagtactgca tcgagaaggt ggagtacgac gtgaagaaca acaggggtgat   2700 cgtgcgcggg aagttcgacc cggagaagct gtgcaagaag atctggtgca aggccggcaa   2760
gatcatcaag gagatcctca tcgtcgacgt ctggccgccg ccgtgcaagc cgccgccgtg   2820
cgagaagcct ccggaggact gcaagcccaa gccctgccat tgctgcagct gcgagaagcc   2880
caagcccaag cccaagccct gccactgcga gaagcccaag ccctgtcact gcgagaagcc   2940
caagccatgc gagaagccgc cgccgaagcc ggagtgcaag ctggtgccgt accccttaccc   3000 ggtgccgtac ccgtacgccg ggcagtggtg ctgcccaaag cctgagccgc cgaagccgcc   3060
gccggagcca ccgaaggagc cggagccgcc gaagccgtgc gggtgctcgc acgccttcgt   3120
gtgcgtctgc aagccggcgc cgccgccgcc gccgccgtgc gggtgctcgg ggggccacgg   3180
gaactgcggc tgcggcatca ggccgtggcc gccgcaggtg tggccgccgc cgccgtctg    3240 cccgccgccg ccgtggtgct acaccgagga caacgccaac gcctgctcca tcatgtgatg   3300
gccggccggc ggccggcgtc gatcacgatc atctctgctg cttaatttcc ttgcttgcta   3360
ctacctctgc tcctttcctt gcctcggaaa tcggaataaa ttaaacacga ggctgatcga   3420
tgtgtttgta attaatccat ggtgtttgtg ttgtgtgctg tgtgggctgt ataataatta   3480
attacagtat gttcatgtaa atttgtttgt ttgtttgttt atgttgttcg atatgtataa   3540
ttatgtacaa taattaatcg tggagaggct cactaaactc ataaactgta gagtatcttg   3600
gctgtaaaag tgtggcaatt tatctttttc ttgtgttagc attggctaca aatagttttt   3660
ggccgtcttt tctcttcgtt tctccccttc tttatgagat taattgtgtg ctgacctaga   3720
tcaaattata gcgcgctgac ctagttttat tgtaactgct cttatggatg tctgctaaca   3780
ccatcaaaca tgattaccgt ggtatatttg tcttaattac tactaactag gactacctag   3840
ggcacccctt gcatatgttt tttttcgaa cgaccagata gatttgagtc atttgactag   3900
cgttatatta ataggaggga aaaaaataca aagtacaaat atccaacagg ccgagaaaag   3960
agaaaaaaaa ctgtacatgc ctacgtgcaa acaagattgc acgaagctct cctcactcct   4020
```

```
catggcaaca ttctcccaat gtgtttagca tcgaaaatac cccaccaacc tcgtcttgga    4080
tgtgactggt catttggtgt attgtcgcct ccttttccct ctgaagattc ttacgttcca    4140
ttccttccaa atttcctagg cgatgagcaa gaaagagat ctgagcccct tttgtttagt    4200
tacttccaag tcgcttgttc cttgtgtcca ccaatgcaag aggtttctac tgtcattcca    4260
tttcagaata agccaattga gaactccaaa ccagatttac ttcgaaacca ggcattcgaa    4320
cataaggtgg tcgacagtgt cgagattccg gattagcaga gttatttggt ttgagagtca    4380
cattcctaca accaatagaa aaccatccta tggaccattt agatagtgtc ctagtatttg    4440
cttttatatt tgctataaat attcttcctt tattgttttt ggagttcaca aacttaataa    4500
tcaaactttg tgatttttta atttccatta acgaattcaa ggaaccacct ttatctctca    4560
tcttcattgc acactactga tttctttcat ccttagggac atatggttga tacgagact    4620 gttttttctat cattatctaa aaaaaatcta aggggcatat atatattgtg ttttctctca    4680
ttcatgcatt tcgcactttt ccctattcgt gaaataccat ttcccacatg agtgcaatgt    4740
ttctt                                                                4745

<210> SEQ ID NO 5
<211> LENGTH: 732
<212> TYPE: DNA
<213> ORGANISM: Oryza sativa

<400> SEQUENCE: 5
atgggtatat tggtcatctt ggtggacctg caatgctgcc gctgcgatgc caagatcagg      60
aaggtcctgg gctgccttga agaggagtac tgcatcgaga aggtggagta cgacgtgaag     120
aacaacaggg tgatcgtgcg cgggaagttc gaccccgaga gctgtgcaa gaagatctgg      180 tgcaaggccg gcaagatcat caaggagatc ctcatcgtcg acgtctggcc gccgccgtgc     240
aagccgccgc cgtgcgagaa gcctccggag gactgcaagc ccaagccctg ccattgctgc     300 agctgccgaga agcccaagcc caagcccaag ccctgccact gcgagaagcc caagccctgt     360
cactgcgaga agcccaagcc atgcgagaag ccgccgccga agccggagtg caagctggtg     420
ccgtacccct tacccggtgcc gtaccccgtac gccgggcagt ggtgctgccc aaagcctgag     480
ccgccgaagc cgccgccgga gccaccgaag gagccggagc cgccgaagcc gtgcgggtgc     540
tcgcacgcct tcgtgtgcgt ctgcaagccg gcgccgccgc cgccgccgcc gtgcgggtgc     600
tcggggggcc acgggaactg cggctgcggc atcaggccgt ggccgccgca ggtgtggccg     660
ccgccgcccg tctgcccgcc gccgccgtgg tgctacaccg aggacaacgc caacgcctgc     720
tccatcatgt ga                                                        732

<210> SEQ ID NO 6
<211> LENGTH: 243
<212> TYPE: PRT
<213> ORGANISM: Oryza sativa

<400> SEQUENCE: 6

Met Gly Ile Leu Val Ile Leu Val Asp Leu Gln Cys Cys Arg Cys Asp
1               5                   10                  15

Ala Lys Ile Arg Lys Val Leu Gly Cys Leu Glu Glu Glu Tyr Cys Ile
            20                  25                  30

Glu Lys Val Glu Tyr Asp Val Lys Asn Asn Arg Val Ile Val Arg Gly
        35                  40                  45

Lys Phe Asp Pro Glu Lys Leu Cys Lys Lys Ile Trp Cys Lys Ala Gly
    50                  55                  60
```

| | | | | | | | | | | | | | | | |
|---|---|---|---|---|---|---|---|---|---|---|---|---|---|---|---|
| Lys | Ile | Ile | Lys | Glu | Ile | Leu | Ile | Val | Asp | Val | Trp | Pro | Pro | Pro | Cys |
| 65 | | | | 70 | | | | | 75 | | | | | 80 | |
| Lys | Pro | Pro | Pro | Cys | Glu | Lys | Pro | Pro | Glu | Asp | Cys | Lys | Pro | Lys | Pro |
| | | | | 85 | | | | | 90 | | | | | 95 | |
| Cys | His | Cys | Cys | Ser | Cys | Glu | Lys | Pro | Lys | Pro | Lys | Pro | Lys | Pro | Cys |
| | | | | 100 | | | | | 105 | | | | | 110 | |
| His | Cys | Glu | Lys | Pro | Lys | Pro | Cys | His | Cys | Glu | Lys | Pro | Lys | Pro | Cys |
| | | | | 115 | | | | | 120 | | | | | 125 | |
| Glu | Lys | Pro | Pro | Lys | Pro | Glu | Cys | Lys | Leu | Val | Pro | Tyr | Pro | Tyr | |
| | 130 | | | | | 135 | | | | | 140 | | | | |
| Pro | Val | Pro | Tyr | Pro | Tyr | Ala | Gly | Gln | Trp | Cys | Cys | Pro | Lys | Pro | Glu |
| 145 | | | | | 150 | | | | | 155 | | | | | 160 |
| Pro | Pro | Lys | Pro | Pro | Glu | Pro | Pro | Lys | Glu | Pro | Glu | Pro | Pro | Lys | |
| | | | 165 | | | | | 170 | | | | | 175 | | |
| Pro | Cys | Gly | Cys | Ser | His | Ala | Phe | Val | Cys | Val | Cys | Lys | Pro | Ala | Pro |
| | | | 180 | | | | | 185 | | | | | 190 | | |
| Pro | Pro | Pro | Pro | Cys | Gly | Cys | Ser | Gly | Gly | His | Gly | Asn | Cys | Gly | |
| | | 195 | | | | | 200 | | | | | 205 | | | |
| Cys | Gly | Ile | Arg | Pro | Trp | Pro | Pro | Gln | Val | Trp | Pro | Pro | Pro | Val | |
| | 210 | | | | | 215 | | | | | 220 | | | | |
| Cys | Pro | Pro | Pro | Pro | Trp | Cys | Tyr | Thr | Glu | Asp | Asn | Ala | Asn | Ala | Cys |
| 225 | | | | | 230 | | | | | 235 | | | | | 240 |
| Ser | Ile | Met | | | | | | | | | | | | | |

<210> SEQ ID NO 7
<211> LENGTH: 975
<212> TYPE: DNA
<213> ORGANISM: Oryza sativa

<400> SEQUENCE: 7

```
gtacgacgtg aagaacaaca gggtgatcgt gcgcgggaag ttcgacccgg agaagctgtg      60
caagaagatc tggtgcaagg ccggcaagat catcaaggag atcctcatcg tcgacgtctg     120
gccgccgccc tgccgcagc cgccgccgcc gtgcaagccg ccgccgtgcg agaagcctcc     180
ggaggactgc aagcccaagc cctgccattg ctgcagctgc gagaagccca gcccaagcc     240
caagccctgc cactgcgaga agcccaagcc ctgtcactgc gagaagccca gccatgcga     300
aagccgccg ccgtgcaagc cggaggagcc gccgaagccg ccgccggaga gccgccgcc     360
gaagccggag tgcaagctgg tgccgtaccc ttacccggtg ccgtacccgt acgccgggca     420
gtggtgctgc ccaaagcctg agccgccgaa gccgccgccg gagccaccga aggagccgga     480
gccgccgaag ccgtgcgggt gctcgcacgc cttcgtgtgc gtctgcaagc cggcgccgcc     540
gccgccgccg ccgtgcgggt gctcgggggg ccacgggaac tgcggctgcg gcatcaggcc     600
gtggccgccg caggtgtggc cgccgccgcc cgtctgcccg ccgccgccgt ggtgctacac     660
cgaggacaac gccaacgcct gctccatcat gtgatggccg gccggcggtc ggcgtcgatc     720
acgatcatct ctgctgctta atttccttgc ttgctactac ctctgctcct ttccttgcct     780
cggaaatcgg aataaattaa acacgaggct gatcgatgtg tttgtaatta atccatggtg     840
tttgtgttgt gtgctgtgtg ggctgtataa taattaatta cagtatgttc atgtaaattt     900
gtttgtttgt ttgtttatgt tgttcgatat gtataattat gtacaataat taatcgtgga     960
gaggctcact aaact                                                      975
```

```
<210> SEQ ID NO 8
<211> LENGTH: 24
<212> TYPE: DNA
<213> ORGANISM: Artificial
<220> FEATURE:
<223> OTHER INFORMATION: an artificially synthesized primer sequence

<400> SEQUENCE: 8
agaaggtgga gtacgacgtg aaga                                          24

<210> SEQ ID NO 9
<211> LENGTH: 25
<212> TYPE: DNA
<213> ORGANISM: Artificial
<220> FEATURE:
<223> OTHER INFORMATION: an artificially synthesized primer sequence

<400> SEQUENCE: 9
agtttagtga gcctctccac gatta                                         25

<210> SEQ ID NO 10
<211> LENGTH: 916
<212> TYPE: DNA
<213> ORGANISM: Oryza sativa

<400> SEQUENCE: 10
agaaggtgga gtacgacgtg aagaacaaca gggtgatcgt gcgcgggaag ttcgacccgg    60
agaagctgtg caagaagatc tggtgcaagg ccggcaagat catcaaggag atcctcatcg   120
tcgacgtctg gccgccgccg tgcaagccgc cgccgtgcga aagcctccg gaggactgca    180 agcccaagcc ctgccattgc tgcagctgcg agaagcccaa gcccaagccc aagccctgcc   240
actgcgagaa gcccaagccc tgtcactgcg agaagcccaa gccatgcgag aagccgccgc   300
cgaagccgga gtgcaagctg gtgccgtacc cttacccggt gccgtacccg tacgccgggc   360
agtggtgctg cccaaagcct gagccgccga agccgccgcc ggagccaccg aaggagccgg   420
agccgccgaa gccgtgcggg tgctcgcacg ccttcgtgtg cgtctgcaag ccggcgccgc   480
cgccgccgcc gccgtgcggg tgctcggggg gccacgggaa ctgcggctgc ggcatcaggc   540
cgtggccgcc gcaggtgtgg ccgccgccgc ccgtctgccc gccgccgccg tggtgctaca   600
ccgaggacaa cgccaacgcc tgctccatca tgtgatggcc ggccggcggc cggcgtcgat   660
cacgatcatc tctgctgctt aatttccttg cttgctacta cctctgctcc tttccttgcc   720
tcggaaatcg gaataaatta aacacgaggc tgatcgatgt gttttgtaatt aatccatggt   780 gtttgtgttg tgtgctgtgt gggctgtata ataattaatt acagtatgtt catgtaaatt   840
tgtttgtttg tttgtttatg ttgttcgata tgtataatta tgtacaataa ttaatcgtgg   900
agaggctcac taaact                                                  916

<210> SEQ ID NO 11
<211> LENGTH: 295
<212> TYPE: DNA
<213> ORGANISM: Oryza sativa

<400> SEQUENCE: 11
tggccggccg gcggtcggcg tcgatcacga tcatctctgc tgcttaattt ccttgcttgc    60
tactacctct gctcctttcc ttgcctcgga atcggaata aattaaacac gaggctgatc   120
gatgtgtttg taattaatcc atggtgtttg tgttgtgtgc tgtgtgggct gtataataat   180
taattacagt atgttcatgt aaatttgttt gtttgtttgt ttatgttgtt cgatatgtat   240
aattatgtac aataattaat cgtggagagg ctcactaaac tcataaactg tagag        295
```

```
<210> SEQ ID NO 12
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 12
ttttcctgag aaatttgtaa aga                                           23

<210> SEQ ID NO 13
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 13
cgtcgacgat gaggatct                                                 18

<210> SEQ ID NO 14
<211> LENGTH: 20
<212> TYPE: DNA
<213> ORGANISM: Artificial
<220> FEATURE:
<223> OTHER INFORMATION: an artificially synthesized primer sequence

<400> SEQUENCE: 14
ctcccaatgt gtttagcatc                                               20

<210> SEQ ID NO 15
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 15
caaccatatg tccctaagga t                                             21

<210> SEQ ID NO 16
<211> LENGTH: 22
<212> TYPE: DNA
<213> ORGANISM: Artificial
<220> FEATURE:
<223> OTHER INFORMATION: an artificially synthesized primer sequence

<400> SEQUENCE: 16
gtacgacgtg aagaacaaca gg                                            22

<210> SEQ ID NO 17
<211> LENGTH: 17
<212> TYPE: DNA
<213> ORGANISM: Artificial
<220> FEATURE:
<223> OTHER INFORMATION: an artificially synthesized primer sequence

<400> SEQUENCE: 17
gcttgggctt gcagtcc                                                  17

<210> SEQ ID NO 18
<211> LENGTH: 21
<212> TYPE: DNA
<213> ORGANISM: Artificial
<220> FEATURE:
<223> OTHER INFORMATION: an artificially synthesized probe sequence
```

```
<400> SEQUENCE: 18
ctgccgcagc cgccgccgcc g                                           21

<210> SEQ ID NO 19
<211> LENGTH: 48
<212> TYPE: DNA
<213> ORGANISM: Artificial
<220> FEATURE:
<223> OTHER INFORMATION: an artificially synthesized probe sequence

<400> SEQUENCE: 19
tgcaagccgg aggagccgcc gaagccgccg ccggagaagc cgccgccg              48

<210> SEQ ID NO 20
<211> LENGTH: 4803
<212> TYPE: DNA
<213> ORGANISM: Oryza sativa

<400> SEQUENCE: 20
tctagatgat gctttatgtg aaggcaataa atgataatta agtgtaatat aatgtatttt    60
ttaaacatcg tagtgaagtc ccatttctag tacgtaatgg atcgaaatgg ggagggactg   120
cttctctttt agaaaaaaat gtaaaattga gatgagcttt tataagacat gtaaggccat   180
atgtctagtg taagtatgat gctagcaagc acattttagc atcttaaaat aaaaggcaag   240
cacattaata ttttaggagt tagcatggat gcaatacagt agaagaggag atgccaacaa   300
aaaagaatat ggaaaatttg tttcatacca tcaaagttcc ctgtgttttg ctttatacca   360
tcagcgtttg tggtgtactt taacaccatc caaagtttgc tccgttacct atccactcca   420
cgaaatgtgc ttgctagcat ggatgaaaaa gtaaccgaaa caaacagttg tggtatactc   480
ctaagtaatc ctaagtagcc accggattca atactttatt ctcaatcgtc cttctagtct   540
attcccaatt atatgggttt gacccgttac aacgtacggg catgttacta gcgtaaggaa   600
agagatggtt tctaaaagag ttttttttt ccaacagtcc tacccaatct atagcgctag   660
acaagaaagc gaaagctaaa cccatattta ttaccgtaat gttgcaaact taatattacc   720
tgcaatagac atgccctaac atggtttcag gaccacaaac cagagctcta aaattccgag   780
cacatgttca gaatatatat acatttttaa ttcccttcta tactactcca acttacctct   840
atggaggtaa gaggctaaaa ttgaaactag ataactgaat gttcttatat ttttcctaat   900
aaaaatataa ttgctccttt catttaatac ttatatcaca acatgtagcc atatgagcca   960
aaactgtatt agccatattt tagcgaataa ggctcaatgc gattctgtgt ctgagctctg  1020
gcctgaaaat tcttgtaact ttatctcaca tatgatgtgt gaggaagctt ctcatgagta  1080
atatattccc tatttccccg caaaaaaaaa acttatatca caacaaaaat ggaaaagacc  1140
aacactgagt attgtagaag ctagtacttt tggcaaatgt gcccgaagat ccccaaaaca  1200
gtttgtggca taattcagaa gattgttagc tcagaaatca tttcagacta ggatattgcc  1260
gacacatcag agttctcgtg taatcaagaa gcaaggaact gtacagtgca gtgatgatat  1320
acaactatag gagaggacga actgatactg acggatgctg tgtgtaaaat atctctgtaa  1380
aatcaggaat actgggagac tgattggatg atagatttat acggtcacaa tcatctcgtt  1440
aaacacactt ttcattaaag aggaattacc aaatacagta attgattcga cggtgccgcg  1500
agaaatgtgc tatatataaa tgctcaccta tatttgggca gattagttaa tttcaggaat  1560
tttccacaga gaaagctaaa tgagtgctaa atgagtcgca ttgcgtacta ctacaagggt  1620
ccaaacagaa attgatatct gaaattagct tttcttaaga taacaatgat attttttttt  1680
```

```
attgaagcac aaggtgtgcc tgaaatcgaa ttctgaaagg tattcttatt tttcagagga    1740
aaatgtacac tggtaccatt ctgaaagcta attgagagat gacaaggcgt gagaaggacc    1800
aaactgtcct atatacatgt ggtcattttc catctcttgc aataggttat caagacccct    1860
cctgaaacat ggaccgtcca gatgcgatcc gacggacgaa aaaaaccaat ggcagaatat    1920
ttcaggctct ggcatatcca aacataaata agtaacataa ggttcagctc tgctccatcc    1980
atgcattgcc tccattattc atgcttcgat tctccatgct ttcctctact gctcattggt    2040
aacattcggc aaatttgaca ggtgagctca gtattttaaa tcttaatgta gtactttggt    2100
gtgctaatcc ttgctctgtt caaaagagaa ttctggtttc tttgctattt tgaaaagaga    2160
attttcgtta caggacttca acttccataa tactttttt tataattaag gcatgatata    2220
tatcttcttt ctgaattcca cgggaattgc acttttcct gagaaatttg taagagcat    2280 gcctgttaat tgcaaggggc ccctaactct gttatgagaa aagagaacta taagatgc    2340 tcaataagca cctcttttt ttttttgtt aactgaccaa agcctgtcta tctgcatttt    2400
tttttgtttt ttgtttttct tgtgtgcaga tgggtatatt ggtcatctcg gtggacctgc    2460
aatgctgccg ctgcgatgcc aagatcagga aggtcctggg ctgccttgaa ggtataataa    2520
attctgcccg aatcgtccat gtttgattga attttcaagg ctaatcagca gtgttcctgc    2580
tcaattggga gcaaaacctc tgttaaaaag ggtgtgtttg aatgaatata attgaatatg    2640
aacgcagagg agtactgcat cgagaaggtg gagtacgacg tgaagaacaa cagggtgatc    2700
gtgcgcggga agttcgaccc ggagaagctg tgcaagaaga tctggtgcaa ggccggcaag    2760
atcatcaagg agatcctcat cgtcgacgtc tggccgccgc cgtcgccgcc gccgtgcaag    2820
ccgccgccgt gcgagaagcc tccggaggac tgcaagccca agccctgcca ttgctgcagc    2880
tgcgagaagc ccaagcccaa gcccaagccc tgccactgcg agaagcccaa gccctgtcac    2940
tgcgagaagc ccaagccatg cgagaagccg ccgccgtgca agccggagga gccgccgaag    3000
ccgccgccgg agaagccgcc gccgaagccg gagtgcaagc tggtgccgta cccttacccg    3060
gtgccgtacc cgtacgccgg gcagtggtgc tgcccaaagc tgagccgcc gaagccgccg    3120 ccggagccac cgaaggagcc ggagccgccg aagccgtgcg ggtgctcgca cgccttcgtg    3180
tgcgtctgca agccggcgcc gccgccgccg ccgccgtgcg ggtgctcggg gggccacggg    3240
aactgcggct gcggcatcag gccgtggccg ccgcaggtgt ggccgccgcc gcccgtctgc    3300
ccgccgccgc cgtggtgcta caccgaggac aacgccaacg cctgctccat catgtgatgg    3360
ccggccggcg gccggcgtcg atcacgatca tctctgctgc ttaatttcct tgcttgctac    3420
tacctctgct cctttccttg cctcggaaat cggaataaat taaacacgag gctgatcgat    3480
gtgtttgtaa ttaatccatg gtgtttgtgt tgtgtgctgt gtgggctgta taataattaa    3540
ttacagtatg ttcatgtaaa tttgtttgtt tgtttgttta tgttgttcga tatgtataat    3600
tatgtacaat aattaatcgt ggagaggctc actaaactca taaactgtag agtatcttgg    3660
ctgtaaaagt gtggcaattt atcttttct tgtgttagca ttggctacaa atagttttg    3720 gccgtctttt ctcttcgttt ctccccttct ttatgagatt aattgtgtgc tgacctagat    3780
caaattatag cgcgctgacc tagttttatt gtaactgctc ttatggatgt ctgctaacat    3840
catcaaacat gattaccgtg gtatatttgt cttaattact actaactagg actacctagg    3900
ggcacccttg catatgtttt tttcgaacg accagataga tttgagtcat ttgactagcg    3960
ttatattaat aggagggaaa aaatacaaag tacaaatatc caacaggccg agaaaagaga    4020
```

-continued

| | |
|---|---|
| aaaaaaactg tacgtgccta cgtgcaaaca agattgcacg aagctctcct cactcctcat | 4080 |
| ggcaacattc tcccaatgtg tttagcatcg aaaatacccc accaacctcg tcttggatgt | 4140 |
| gattggtcat ttggtgtatt gtcgcctcct tttccctctg aagattctta tgttccattc | 4200 |
| cttccaaatt tcctaggcga tgagcaagaa aagagatctg agcccttttt gtttagttac | 4260 |
| ttccaagtcg cttgttcctt gtgtccacca atgtaagagg tttctactgt cattccattt | 4320 |
| cagaataagc caattgagaa ctccaaacca gatttacttc gaaaccaggc attcgaatat | 4380 |
| aaggtggtcg acagtttcga gattccggat tagcagagtt attggtttg agagtcacat | 4440 |
| tcctacaacc aatagaaaac catcctatgg accatttaga taatgtccta gtatttgctt | 4500 |
| ttatatttgc tataaatatt cttcctttat tgttttggga gttcacaaac ttaataatca | 4560 |
| aactttgtga ttttttaatt tccattaacg aattcaagga accacctta tctctcatct | 4620 |
| tcattgcaca ctactgattt cttcatcct tagggatata tggttgatac ggagactgtt | 4680 |
| tttctatcat tatctaaaaa aaatctaag gggcatatat atattgtgtt ttctctcatt | 4740 |
| catgcatttc gcacttttcc ctattcgtga ataccatttt cccacatgag tgcaatgttt | 4800 |
| ctt | 4803 |

<210> SEQ ID NO 21
<211> LENGTH: 1014
<212> TYPE: DNA
<213> ORGANISM: Oryza sativa

<400> SEQUENCE: 21

| | |
|---|---|
| atgggtatat tggtcatctc ggtggacctg caatgctgcc gctgcgatgc caagatcagg | 60 |
| aaggtcctgg gctgccttga agaggagtac tgcatcgaga aggtggagta cgacgtgaag | 120 |
| aacaacaggg tgatcgtgcg cgggaagttc gacccggaga agctgtgcaa gaagatctgg | 180 |
| tgcaaggccg gcaagatcat caaggagatc ctcatcgtcg acgtctggcc gccgccgtcg | 240 |
| ccgccgccgt gcaagccgcc gccgtgcgag aagcctccgg aggactgcaa gcccaagccc | 300 |
| tgccattgct gcagctgcga gaagcccaag cccaagccca gccctgcca ctgcgagaag | 360 |
| cccaagccct gtcactgcga gaagcccaag ccatgcgaga gccgccgcc gtgcaagccg | 420 |
| gaggagccgc cgaagccgcc gccggagaag ccgccgccga gccggagtg caagctggtg | 480 |
| ccgtacccct tacccggtgcc gtacccgtac gccgggcagt ggtgctgccc aaagcctgag | 540 |
| ccgccgaagc cgccgccgga ccaccgaag gagccggagc cgccgaagcc gtgcgggtgc | 600 |
| tcgcacgcct tcgtgtgcgt ctgcaagccg gcgccgccgc cgccgccgcc gtgcgggtgc | 660 |
| tcggggggcc acgggaactg cggctgcggc atcaggccgt ggccgccgca ggtgtggccg | 720 |
| ccgccgcccg tctgcccgcc gccgccgtgg tgctacaccg aggacaacgc caacgcctgc | 780 |
| tccatcatgt gatggccggc cggcggccgg cgtcgatcac gatcatctct gctgcttaat | 840 |
| ttccttgctt gctactacct ctgctccttt ccttgcctcg gaaatcggaa taaattaaac | 900 |
| acgaggctga tcgatgtgtt tgtaattaat ccatggtgtt tgtgttgtgt gctgtgtggg | 960 |
| ctgtataata attaattaca gtatgttcat gtaaatttgt tgtttgtttt gttt | 1014 |

<210> SEQ ID NO 22
<211> LENGTH: 263
<212> TYPE: PRT
<213> ORGANISM: Oryza sativa

<400> SEQUENCE: 22

```
Met Gly Ile Leu Val Ile Leu Val Asp Leu Gln Cys Cys Arg Cys Asp
1               5                   10                  15

Ala Lys Ile Arg Lys Val Leu Gly Cys Leu Glu Glu Glu Tyr Cys Ile
            20                  25                  30

Glu Lys Val Glu Tyr Asp Val Lys Asn Asn Arg Val Ile Val Arg Gly
        35                  40                  45

Lys Phe Asp Pro Glu Lys Leu Cys Lys Lys Ile Trp Cys Lys Ala Gly
    50                  55                  60

Lys Ile Ile Lys Glu Ile Leu Ile Val Asp Val Trp Pro Pro Pro Ser
65                  70                  75                  80

Pro Pro Pro Cys Lys Pro Pro Cys Glu Lys Pro Pro Glu Asp Cys
                85                  90                  95

Lys Pro Lys Pro Cys His Cys Cys Ser Cys Glu Lys Pro Lys Pro Lys
                100                 105                 110

Pro Lys Pro Cys His Cys Glu Lys Pro Lys Pro Cys His Cys Glu Lys
            115                 120                 125

Pro Lys Pro Cys Glu Lys Pro Pro Cys Lys Pro Glu Glu Pro Pro
        130                 135                 140

Lys Pro Pro Glu Lys Pro Pro Lys Pro Glu Cys Lys Leu Val
145                 150                 155                 160

Pro Tyr Pro Tyr Pro Val Pro Tyr Pro Tyr Ala Gly Gln Trp Cys Cys
                165                 170                 175

Pro Lys Pro Glu Pro Pro Lys Pro Pro Glu Pro Pro Lys Glu Pro
            180                 185                 190

Glu Pro Pro Lys Pro Cys Gly Cys Ser His Ala Phe Val Cys Val Cys
        195                 200                 205

Lys Pro Ala Pro Pro Pro Pro Pro Cys Gly Cys Ser Gly Gly His
    210                 215                 220

Gly Asn Cys Gly Cys Gly Ile Arg Pro Pro Pro Gln Val Trp Pro
225                 230                 235                 240

Pro Pro Pro Val Cys Pro Pro Pro Pro Trp Cys Tyr Thr Glu Asp Asn
                245                 250                 255

Ala Asn Ala Cys Ser Ile Met
                260
```

<210> SEQ ID NO 23
<211> LENGTH: 976
<212> TYPE: DNA
<213> ORGANISM: Oryza sativa

<400> SEQUENCE: 23

```
agaaggtgga gtacgacgtg aagaacaaca gggtgatcgt gcgcgggaag ttcgacccgg      60
agaagctgtg caagaagatc tggtgcaagg ccggcaagat catcaaggag atcctcatcg     120
tcgacgtctg gccgccgccg tcgccgccgc cgtgcaagcc gccgccgtgc gagaagcctc     180
cggaggactg caagcccaag ccctgccatt gctgcagctg cgagaagccc aagcccaagc     240
ccaagccctg ccactgcgag aagcccaagc cctgtcactg cgagaagccc aagccatgcg     300
agaagccgcc gccgtgcaag ccggaggagc cgccgaagcc gccgccggag aagccgccgc     360
cgaagccgga gtgcaagctg gtgccgtacc cttacccggt gccgtacccg tacgccgggc     420
agtggtgctg cccaaaagcct gagccgccga agccgccgcc ggagccaccg aaggagccgg     480
agccgccgaa gccgtgcggg tgctcgcacg ccttcgtgtg cgtctgcaag ccggcgccgc     540
cgccgccgcc gccgtgcggg tgctcggggg gccacgggaa ctgcggctgc ggcatcaggc     600
```

```
cgtggccgcc gcaggtgtgg ccgccgccgc ccgtctgccc gccgccgccg tggtgctaca    660
ccgaggacaa cgccaacgcc tgctccatca tgtgatggcc ggccggcggc cggcgtcgat    720
cacgatcatc tctgctgctt aatttccttg cttgctacta cctctgctcc tttccttgcc    780
tcggaaatcg gaataaatta aacacgaggc tgatcgatgt gtttgtaatt aatccatggt    840
gtttgtgttg tgtgctgtgt gggctgtata ataattaatt acagtatgtt catgtaaatt    900
tgtttgtttg tttgtttatg ttgttcgata tgtataatta tgtacaataa ttaatcgtgg    960
agaggctcac taaact                                                    976

<210> SEQ ID NO 24
<211> LENGTH: 222
<212> TYPE: DNA
<213> ORGANISM: Oryza sativa

<400> SEQUENCE: 24
tggccggccg gcggccggcg tcgatcacga tcatctctgc tgcttaattt ccttgcttgc     60
tactacctct gctcctttcc ttgcctcgga aatcggaata aattaaacac gaggctgatc    120
gatgtgtttg taattaatcc atggtgtttg tgttgtgtgc tgtgtgggct gtataataat    180
taattacagt atgttcatgt aaatttgttt gtttgtttgt tt                       222

<210> SEQ ID NO 25
<211> LENGTH: 12
<212> TYPE: DNA
<213> ORGANISM: Oryza sativa

<400> SEQUENCE: 25
tcgccgccgc cg                                                         12

<210> SEQ ID NO 26
<211> LENGTH: 23
<212> TYPE: DNA
<213> ORGANISM: Artificial
<220> FEATURE:
<223> OTHER INFORMATION: an artificially synthesized primer sequence

<400> SEQUENCE: 26
gatcctcatc gtcgacgtct ggc                                             23

<210> SEQ ID NO 27
<211> LENGTH: 19
<212> TYPE: DNA
<213> ORGANISM: Artificial
<220> FEATURE:
<223> OTHER INFORMATION: an artificially synthesized primer sequence

<400> SEQUENCE: 27
agggtacggc accagcttg                                                  19
```

RICE BLAST SUSCEPTIBILITY GENE PI21, RESISTANCE GENE PI21, AND USES THEREOF

RELATED APPLICATIONS

The present application is a divisional application of U.S. application Ser. No. 11/922,994, filed Apr. 24, 2008, which is a 35 U.S.C. 371 national stage filing of International Application No. PCT/JP2006/311341, filed Jun. 6, 2006, which claims priority to Japanese Application No. 2005-187867, filed Jun. 28, 2005. The entire contents of each of these applications are hereby incorporated by reference herein.

TECHNICAL FIELD

The present invention relates to pi21, a gene conferring rice with blast field resistance, and methods for modifying field resistance to blast in plants by using the gene.

BACKGROUND ART

Resistance of rice to blast fungi is classified into two types: true resistance and field resistance (Non-patent Document 1). The former is based on hypersensitive reactions, and is a very effective and qualitative resistance highly specific to race. It has been known by experience that a variety introduced with a single resistance gene loses its effect in a few years due to the appearance of fungi compatible with the gene. On the other hand, field resistance is defined as the difference of resistance among varieties that is observed under conditions where true resistance is not functioning. Although the effect of field resistance is smaller compared to true resistance, it is practically useful because it has low race specificity and can confer continuous resistance to varieties.

Thirty or more kinds of genes associated with true resistance are known, and of these, Pib and Pita genes have been isolated (Non-patent Document 2). It has been found that these genes are NBS-LRR class genes having nucleotide binding sites (NBS) and leucine-rich repeats (LRRs), with structures similar to previously reported plant disease resistance genes. Like other disease resistance genes, products of plant resistance genes are considered to have a receptor function, directly or indirectly recognizing products of nonpathogenic genes in pathogens corresponding to the diseases. It has been actually revealed that Pita physically and directly binds to a nonpathogenic gene product.

As for field resistance, Japanese upland rice varieties are known to have excellent traits, and chromosomal positions of multiple gene loci involved in field resistance have been identified (Non-patent Document 3). However, the structure and expression mechanisms of the genes have not been elucidated, and thus field resistance cannot yet be efficiently used for breeding selection compared to true resistance. Multiple chromosome regions in the West Africa upland rice variety *Moroberekan* have been reported to play a role in incomplete resistance, which is a concept similar to field resistance (Non-patent Document 4); however, no genes have been identified.

[Patent Document 1] Japanese Patent Application Kokai Publication No. (JP-A) 2000-93028 (unexamined, published Japanese patent application)
[Patent Document 2] JP-A 2000-342262
[Patent Document 3] (Granted/Registered) Japanese Patent No. 3376453 (P3376453)
[Patent Document 4] JP-A 2003-88379 (P2003-88379A)
[Patent Document 5] JP-A 2003-199577 (P2003-199577A)
[Patent Document 6] JP-A 2003-199448 (P2003-199448A)
[Patent Document 7] JP-A 2004-329215 (P2004-329215A)
[Non-patent Document 1] Rice Blast and Breeding for its resistance. Kousaka and Yamazaki eds., p 175-186, 1980, Hakuyusha
[Non-patent Document 2] Wang et al., Plant J 19:55-64, 1999; Bryan et al. Plant Cell. 12: 2033-46, 2000
[Non-patent Document 3] Fukuoka and Okuno, Theor Appl Genet. 03:185-190, 2001
[Non-patent Document 4] Wang et al., Genet 136:1421-1434, 1994

DISCLOSURE OF THE INVENTION

[Problems to be Solved by the Invention]

The present invention was accomplished under such circumstances. The problems to be solved by the present invention are to isolate and identify genes involved in field resistance to blast by map-based cloning, and to provide methods for modifying blast field resistance in plants using the genes.

[Means for Solving the Problems]

The present invention relates to genes controlling blast resistance in plants. The allele pi21 of the Pi21 gene was known to confer rice (*Oryza sativa* L.) with field resistance to blast and to exist at some position in the vast region of rice chromosome 4. The present inventors aimed to elucidate the existence region and to isolate the gene as a single gene.

First, the present inventors performed a detailed linkage analysis of the pi21 region using a large-scale segregating population indispensable for map-based cloning, in order to create a genetic map of the pi21 region. The inventors obtained a backcross population by continuously backcrossing a paddy rice variety, *Nipponbare* or *Aichi Asahi*, comprising a susceptibility allele Pi21 which does not suppress blotch progression, with a Japanese upland rice variety, *Owarihatamochi* comprising a resistance allele pi21 which suppresses blotch progression. When a linkage analysis with RFLP markers was performed for the obtained backcross population, it was confirmed that the pi21 gene locus is located between the RFLP markers G271 and G317.

Next, using the RFLP markers RA3591 and 13S1, which are located on each side of the pi21 locus, the present inventors selected organisms with chromosomal recombination near the pi21 locus in order to create a more accurate genetic map of the pi21 region. The present inventors also selected organisms with chromosomal recombination near the pi21 locus, by searching an F2 population obtained by crossing a line having the resistance allele from *Owarihatamochi* with a line having the genetic background of a Japanese paddy rice variety and the susceptibility allele from the Indian paddy rice variety *Kasalath*. As a result of creating a detailed linkage map using these organisms and the produced DNA markers, the pi21 gene locus turned out to be located in the genomic region of about 25 kb sandwiched between the SSCP marker Pa102484 and the SNP marker P702D3_#12. Further, the nucleotide sequence of PAC clone P702D03 that was considered to include the pi21 gene was determined. Moreover, by analyzing the nucleotide sequence of the 25-kb candidate genomic region in the resistant variety *Owarihatamochi* and the susceptibility varieties *Aichi Asahi* and *Kasalath*, it was found that the pi21 gene is located in the genomic region of about 1.8 kb sandwiched between the SNP markers P702D03_#38 and P702D03_#80.

Thus, the present inventors designed primers that could amplify a corresponding portion using the already obtained nucleotide sequence information of *Nipponbare*, and then compared the nucleotide sequences of the genomic PCR and RT-PCR products between the susceptibility varieties *Nip-*

*ponbare* and *Aichi Asahi* and the resistant variety *Owarihatamochi*. As a result, it was found that there are two DNA mutations in the exon region of the gene in the resistant variety compared to the susceptibility varieties. It was demonstrated that in contrast to the susceptibility varieties, the resistant variety has deletions of 7 amino acids and 16 amino acids, and that these mutations are related to blotch progression caused by blast infection. That is, the present invention relates to the pi21 gene that controls plant resistance to blast, and specifically provides the following inventions:

[1] a DNA of any one of the following (a) to (h):
  (a) a DNA that encodes a protein comprising the amino acid sequence of SEQ ID NO: 3 or 22,
  (b) a DNA comprising a coding region of the nucleotide sequence of SEQ ID NO: 1, 2, 20, or 21,
  (c) a DNA encoding a protein which comprises an amino acid sequence with a substitution, deletion, addition, and/or insertion of one or more amino acids in the amino acid sequence of SEQ ID NO: 3 or 22, and which has a function equivalent to that of a protein comprising the amino acid sequence of SEQ ID NO: 3 or 22,
  (d) a DNA which hybridizes under stringent conditions to a DNA comprising the nucleotide sequence of SEQ ID NO: 1, 2, 20, or 21, and which encodes a protein having a function equivalent to that of a protein comprising the amino acid sequence of SEQ ID NO: 3 or 22,
  (e) a DNA that encodes a protein comprising the amino acid sequence of SEQ ID NO: 6,
  (f) a DNA comprising a coding region of the nucleotide sequence of SEQ ID NO: 4 or 5,
  (g) a DNA encoding a protein which comprises an amino acid sequence with a substitution, deletion, addition, and/or insertion of one or more amino acids in the amino acid sequence of SEQ ID NO: 6, and which has a function equivalent to that of a protein comprising the amino acid sequence of SEQ ID NO: 6, and
  (h) a DNA which hybridizes under stringent conditions to a DNA comprising the nucleotide sequence of SEQ ID NO: 4 or 5, and which encodes a protein having a function equivalent to that of a protein comprising the amino acid sequence of SEQ ID NO: 6;

[2] a DNA of any one of the following (i) to (iv), having an ability to confer plants with field resistance to blast:
  (i) a DNA that encodes an RNA complementary to a transcription product of the DNA of any one of (a) to (d) in [1],
  (ii) a DNA that encodes an RNA having the ribozyme activity to specifically cleave a transcription product of the DNA of any one of (a) to (d) in [1],
  (iii) a DNA that encodes an RNA which inhibits expression of the DNA of any one of (a) to (d) in [1] by a co-suppression effect, and
  (iv) a DNA that encodes an RNA having RNAi activity to specifically cleave a transcription product of the DNA of any one of (a) to (d) in [1];

[3] the DNA of [2], wherein the plant is rice, wheat, barley, oat, corn, Job's tears, Italian ryegrass, perennial ryegrass, timothy, meadow fescue, millet, foxtail millet, or sugarcane;

[4] a vector comprising the DNA of any one of [1] to [3];

[5] a transformed cell that maintains the DNA of any one of [1] to [3] in an expressible state;

[6] a transformed plant cell into which the DNA of any one of (a) to (d) in [1] has been introduced;

[7] a transformed plant cell into which the DNA of [2] or [3] has been introduced;

[8] the transformed plant cell of [6] or [7], wherein the plant is rice, wheat, barley, oat, corn, Job's tears, Italian ryegrass, perennial ryegrass, timothy, meadow fescue, millet, foxtail millet, or sugarcane;

[9] a transformed plant comprising the transformed cell of any one of [6] to [8];

[10] a transformed plant that is a progeny or clone of the transformed plant of [8];

[11] a propagation material of the transformed plant of [9] or [10];

[12] a method for producing the transformed plant of [9] or [10], which comprises the step of introducing into a plant cell the DNA of any one of (a) to (d) in [1] or the DNA of [2] or [3], and then regenerating a plant from the plant cell;

[13] a method for conferring a plant with field resistance to blast, which comprises the step of expressing the DNA of [2] or [3] in a cell of the plant;

[14] the method of [13], wherein the plant is rice, wheat, barley, oat, corn, Job's tears, Italian ryegrass, perennial ryegrass, timothy, meadow fescue, millet, foxtail millet, or sugarcane;

[15] a protein encoded by the DNA of any one of (a) to (d) in [1];

[16] a method for producing the protein of [15], which comprises the step of culturing a transformed cell comprising a vector that comprises the DNA of any one of (a) to (d) in [1], and then collecting a recombinant protein from the cell or its culture supernatant;

[17] an antibody that binds to the protein of [15];

[18] a DNA comprising at least 15 consecutive nucleotides complementary to the DNA of [1] or a complementary sequence thereof;

[19] an agent that increases field resistance to blast in a plant, which comprises any one of the DNA of [2] or [3] or the vector comprising the DNA;

[20] a primer set that amplifies all or a part of the nucleotide sequence of SEQ ID NO: 1, 4, or 20;

[21] a primer set, that is at least any one of the following (a) to (c):
  (a) a DNA comprising the nucleotide sequence of SEQ ID NO: 8, and a DNA comprising the nucleotide sequence of SEQ ID NO: 9,
  (b) a DNA comprising the nucleotide sequence of SEQ ID NO: 16, and a DNA comprising the nucleotide sequence of SEQ ID NO: 17, and
  (c) a DNA comprising the nucleotide sequence of SEQ ID NO: 26, and a DNA comprising the nucleotide sequence of SEQ ID NO: 27;

[22] a DNA comprising the nucleotide sequence of SEQ ID NO: 7, 10, 18, 19, 23, or 25;

[23] a method comprising the following steps (a) to (c):
  (a) preparing a DNA sample from a test plant,
  (b) amplifying the DNA region described in [1] from the DNA sample, and
  (c) comparing the molecular weight or the nucleotide sequence of the amplified DNA fragment with that of the DNA of (e) or (f) in [1],
which is a method that judges the test plant to have field resistance to blast when the molecular weight or nucleotide sequence is consistent with that of the DNA of (e) or (f) in [1];

[24] a method comprising the following steps (a) to (d):
  (a) preparing a DNA sample from a test plant,
  (b) amplifying the DNA region described in [1] from the DNA sample, (c) separating the amplified double-stranded DNA on a non-denaturating gel, and
(d) comparing the mobility of the separated double-stranded DNA on the gel with that of the DNA of (e) or (f) in [1],
which is a method that judges the test plant to have field resistance to blast when the mobility on the gel is consistent with that of the DNA of (e) or (f) in [1];

[25] a method comprising the following steps (a) to (e):
(a) preparing a DNA sample from a test plant,
(b) amplifying the DNA region described in [1] from the DNA sample,
(c) dissociating the amplified DNA into single-stranded DNAs,
(d) separating the dissociated single-stranded DNAs on a non-denaturating gel, and
(e) comparing the mobility of the separated single-stranded DNAs on the gel with that of the DNA of (e) or (f) in [1],
which is a method that judges the test plant to have field resistance to blast when the mobility on the gel is consistent with the DNA of (e) or (f) in [1];

[26] a method comprising the following steps (a) to (d):
(a) preparing a DNA sample from a test plant,
(b) amplifying the DNA region described in [1] from the DNA sample,
(c) separating the amplified DNA on a gel with a gradually increasing concentration of a DNA denaturant, and
(d) comparing the mobility of the separated DNA on the gel, with that of the DNA of (e) or (f) in [1],
which is the method that judges the test plant to have field resistance to blast when the mobility on the gel is consistent with that of the DNA of (e) or (f) in [1];

[27] a method for selecting a plant having field resistance to blast, which comprises the following steps (a) and (b):
(a) producing a hybrid variety by crossing a plant having field resistance to blast with a plant having an arbitrary function, and
(b) judging whether the plant produced in step (a) has field resistance to blast by the method of any one of [23] to [26];

[28] a method for judging a test rice plant to have field resistance to blast when a molecular marker linked to the DNA of [1] shows the same genotype as that in a rice plant having field resistance to blast;

[29] the method of [28], wherein the molecular marker comprises the DNA of SEQ ID NO: 10;

[30] a method for selecting a rice plant having field resistance to blast, wherein the method comprises the following steps (a) and (b):
(a) producing a hybrid variety by crossing a rice plant having field resistance to blast with a rice plant having an arbitrary function, and
(b) judging whether the rice plant produced in step (a) has field resistance to blast using the method of [28] or [29];

[31] a method of screening for an agent that prevents or ameliorates blast in a plant, wherein the method comprises the following steps (a) to (c):
(a) contacting a test compound with a transcription product of the DNA of any one of (a) to (d) in [1],
(b) detecting the binding of the transcription product of the DNA of any one of (a) to (d) in [1] to the test compound, and
(c) selecting a test compound that binds to the transcription product of the DNA of any one of (a) to (d) in [1];

[32] a method of screening for an agent that prevents or ameliorates blast in a plant, wherein the method comprises the following steps (a) to (c):
(a) contacting a test compound with a cell collected from a plant,
(b) measuring the expression level of a transcription product of the DNA of any one of (a) to (d) in [1], and
(c) selecting a test compound that decreases the expression level of the transcription product as compared to when the test compound is not contacted;

[33] a method of screening for an agent that prevents or ameliorates blast in a plant, which comprises the following steps (a) to (d):
(a) providing a cell or cell extract comprising a DNA in which a reporter gene is operably linked downstream of a promoter region of the DNA of any one of (a) to (d) in [1],
(b) contacting a test compound with the cell or cell extract,
(c) measuring the expression level of the reporter gene in the cell or cell extract, and
(d) selecting a test compound that decreases the expression level of the reporter gene as compared to when the test compound is not contacted;

[34] a method of screening for an agent that prevents or ameliorates blast in a plant, which comprises the following steps (a) to (d):
(a) regenerating a transformed plant from the transformed plant cell of [6],
(b) contacting the blast fungus and a test compound with the transformed plant, and
(c) selecting a test compound that suppresses blast in the transformed plant as compared to when the test compound is not contacted; and

[35] a kit for use in the screening method of any one of [31] to [34].

BRIEF DESCRIPTION OF THE DRAWINGS

FIGS. 2A and 2B show the genetic maps created using segregating populations of 72 samples and 1014 samples. FIG. 2C shows the alignment map with PAC clones of *Nipponbare*. FIG. 2D shows a detailed genetic map of the pi21 gene region, and indicates a candidate genomic region.

BEST MODE FOR CARRYING OUT THE INVENTION

Figure 1:
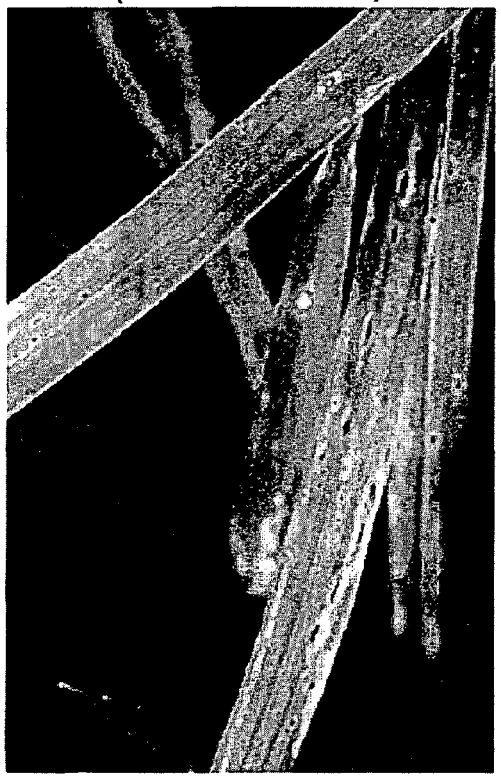
FIG. 1 shows photographs indicating blotches of blast on the line AA-pi21 having the pi21 gene with the genetic background of *Aichi Asahi* (left), and those on *Aichi Asahi* (right).
Figure 1:
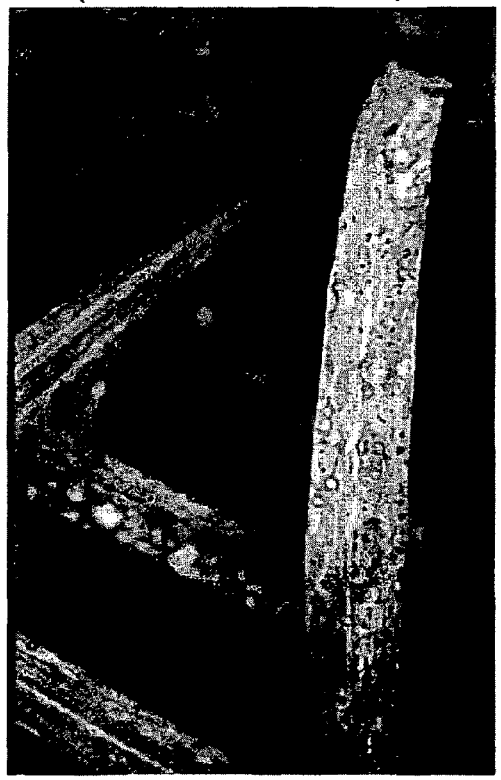

The pi21 gene, an allele of the susceptibility gene Pi21 which does not suppress the progression of rice blast, was until now known to be located somewhere in the vast region of rice chromosome 4, as a gene that confers rice with field resistance to blast. By using the map-based cloning technique, the present inventors narrowed down the pi21 gene region on rice chromosome 4, and finally succeeded in identifying it as a single gene. Moreover, they also succeeded in isolating the Pi21 gene, an allele of the pi21 gene.

As used herein, the term "blast" means the discoloring or necrotization of a plant, or part of a plant infected with a blast fungus, or a pathological feature (blotch) recognized thereby. The blotches of blast appear in every part of the plant, and blast is called seedling blast, leaf blast, panicle blast, spikelet blast, node blast, and leaf node (ligule) blast and such, according to the part where the blotches appear. "Blast" in the present invention includes blast occurring on any of these parts. A "rice blast fungus" which causes blast in rice is called *Magnaporthe grisea* or *Magnaporthe oryzae*, although there is no unified scientific name at present. Moreover, the blast fungus has a teleomorph name, *Magnaporthe oryzae*, and a corresponding anamorph name, *Pyricularia oryzae*, which are used depending on the situation. The blast fungus in the present invention includes all these blast fungi, regardless of their names.

As used herein, the term "blast susceptibility" means the property of a plant to be infected with blast (sometimes means that the symptoms are significant). The term "field resistance to blast" means the difference in symptoms or the property of suppressing the number or size of blotches, which are recognized as the difference in the number or size of blotches between varieties or lines (within the same plant species) when plants are infected with the blast fungus. The term "true resistance" means the property of a plant to cause cell death by a hypersensitive reaction in cells invaded by the blast fungus to prevent infection.

The present invention provides the blast susceptibility gene Pi21, involved in blast of plants, and pi21, a gene conferring field resistance to blast.

More specifically, the Pi21 gene of the present invention comprises the following:

(a) a DNA encoding a protein comprising the amino acid sequence of SEQ ID NO: 3 or 22;

(b) a DNA comprising the coding region of the nucleotide sequence of SEQ ID NO: 1, 2, 20, or 21;

(c) a DNA encoding a protein which comprises an amino acid sequence with a substitution, deletion, addition, and/or insertion of one or more amino acids in the amino acid sequence of SEQ ID NO: 3 or 22, and which has a function equivalent to that of a protein comprising the amino acid sequence of SEQ ID NO: 3 or 22; and (d) a DNA which hybridizes with a DNA comprising the nucleotide sequence of SEQ ID NO: 1, 2, 20, or 21 under a stringent condition, and which encodes a protein having the function equivalent to a protein comprising the amino acid sequence of SEQ ID NO: 3 or 22.

Furthermore, the pi21 gene of the present invention specifically comprises the following:

(a) a DNA encoding a protein comprising the amino acid sequence of SEQ ID NO: 6;

(b) a DNA comprising the coding region of the nucleotide sequence of SEQ ID NO: 4 or 5;

(c) a DNA encoding a protein which comprises an amino acid sequence with a substitution, deletion, addition, and/or insertion of one or more amino acids in the amino acid sequence of SEQ ID NO: 6, and which has the function equivalent to that of a protein comprising the amino acid sequence of SEQ ID NO: 6; and (d) a DNA which hybridizes with a DNA comprising the nucleotide sequence of SEQ ID NO: 4 or 5 under a stringent condition, and which encodes a protein having the function equivalent to a protein comprising the amino acid sequence of SEQ ID NO: 6.

By using the Pi21 gene or the pi21 gene of the present invention, it becomes possible, for example, to prepare recombinant proteins or generate transformed plants with modified field resistance to blast.

In the present invention, plants from which the genes of the present invention are derived include, but are not particularly limited to, for example, monocotyledons such as rice, corn, wheat, barley, oat, Job's tears, Italian ryegrass, perennial ryegrass, timothy, meadow fescue, millet, foxtail millet, sugarcane, and pearl millet; and dicotyledons such as rapeseed, soybean, cotton, tomato, and potato. They also include flowering plants such as chrysanthemum, rose, carnation, and cyclamen, but are not particularly limited thereto.

There is no particular restriction on the forms of the "Pi21 gene" and the "pi21 gene" of the present invention, as long as they can encode the "Pi21 protein" and "pi21 protein", respectively; and the "Pi21 gene" and the "pi21 gene" each comprises a genomic DNA, chemically synthesized DNA and so on as well as a cDNA. Moreover, the Pi21 gene and the pi21 gene comprise a DNA with any nucleotide sequence based on genetic code degeneracy, as long as they encode the Pi21 protein and the pi21 protein, respectively.

One skilled in the art can prepare genomic DNAs and cDNAs by using conventional means. Genomic DNAs can be prepared, for example, by extracting genomic DNAs from a plant; constructing a genomic library (a plasmid, phage, cosmid, BAC, PAC or the like can be used as a vector); developing it; and performing colony hybridization or plaque hybridization using a probe prepared based on the Pi21 gene or the pi21 gene (for example, the DNA of any one of SEQ ID NO: 1, 2, 4, 5, 20, or 21). Alternatively, genomic DNAs can be prepared by preparing primers specific for the Pi21 gene or the pi21 gene and performing PCR by using these primers. cDNAs can be prepared, for example, by synthesizing cDNAs based on mRNAs extracted from a plant; inserting them into vectors such as λZAP to create a cDNA library; developing it; and performing colony hybridization or plaque hybridization as described above. They can also be prepared by performing PCR.

Further, since the Pi21 gene or the pi21 gene is considered to be widely present in the plant kingdom, the Pi21 gene or the pi21 gene also includes not only genes in rice but also homologous genes present in various plants. Herein, the term "homologous gene" refers to a gene in various plants that encodes a protein having a physiological function (for example, blast susceptibility or field resistance to blast) similar to that of the Pi21 gene product or the pi21 gene product in rice.

Methods for isolating homologous genes well known to one skilled in the art include the hybridization technique (Southern E. M., Journal of Molecular Biology, Vol. 98, 503, 1975) and the polymerase chain reaction (PCR) technique (Saiki, R. K., et al. Science, vol. 230, 1350-1354, 1985; Saiki, R. K. et al. Science, vol. 239, 487-491, 1988). Specifically, one skilled in the art can usually isolate homologous genes of the Pi21 gene or the pi21 gene from various plants, by using as a probe the nucleotide sequences (for example, the sequence of any one of SEQ ID NO: 1, 2, 4, 5, 20, or 21) of the rice Pi21 gene or pi21 gene, or a part of it, or by using as primers oligonucleotides which specifically hybridize to the Pi21 gene or the pi21 gene.

In order to isolate DNAs encoding such homologous genes, the hybridization reaction is usually performed under stringent conditions. Examples of stringent hybridization conditions include the conditions of 6 M urea, 0.4% SDS, and 0.5×SSC, or hybridization conditions of equivalent stringency. Isolation of DNAs with higher homology can be expected by using conditions with higher stringency, for example, 6 M urea, 0.4% SDS, and 0.1×SSC. The sequences of the isolated DNAs can be determined by a known method. Homology of isolated DNAs indicates a sequence identity of at least 50% or more, more preferably 70% or more, still more preferably 90% or more (for example, 95%, 96%, 97%, 98%, 99% or more) over the entire amino acid sequence. Sequence homology can be determined using the programs of BLASTN (nucleic acid level) or BLASTX (amino acid level) (Altschul et al. J. Mol. Biol. 215: 403-410, 1990). The programs are based on the algorithm BLAST by Karlin and Altschul (Proc. Natl. Acad. Sci. USA, 87: 2264-2268, 1990; Proc. Natl. Acad. Sci. USA, 90: 5873-5877, 1993). When analyzing a nucleotide sequence by BLASTN, parameters are set to, for example, score=100 and wordlength=12. When analyzing an amino acid sequence by BLASTX, parameters are, for example, set to score=50 and wordlength=3. Alternatively, an amino acid sequence can be analyzed using Gapped BLAST program as indicated by Altschul et al. (Nucleic Acids Res. 25: 3389-3402, 1997). When BLAST and Gapped BLAST programs are used, the default parameters of each program are used. The specific procedures of these analysis methods are known.

The present invention also provides the following DNAs that are used to suppress the plant endogenous Pi21 gene expression:

(a) a DNA encoding an RNA complementary to a transcription product of the Pi21 gene, (b) a DNA encoding an RNA that has the ribozyme activity to specifically cleave a transcription product of the Pi21 gene, (c) a DNA encoding an RNA which inhibits Pi21 gene expression by a co-suppression effect, and (d) a DNA encoding an RNA that has the RNAi activity to specifically cut a transcription product of the Pi21 gene.

These DNAs can suppress blotch progression by blast in plants.

In the present invention, plants in which the Pi21 gene expression is suppressed are not particularly limited, and any plant desired to be conferred field resistance to blast can be used; however, agricultural crops and ornamental plants are suitable from an industrial viewpoint. Useful agricultural crops include, but are not particularly limited to, monocotyledons such as rice, corn, wheat, barley, oats, Job's tears, Italian ryegrass, perennial ryegrass, timothy, meadow fescue, millet, foxtail millet, sugarcane, and pearl millet; and dicotyledons such as rapeseed, soybean, cotton, tomato, and potato. Ornamental plants include flowering plants such as chrysanthemum, rose, carnation, and cyclamen, but are not limited thereto. Plants susceptible to the rice blast fungus include pasture grasses such as barley, Italian ryegrass, and meadow fescue; and corn. In addition, many plants have been reported as those which the blast fungus separated from rice can parasitize, including tribe Oryzeae such as *Leersia oryzoides* and wild rice; tribe Poeae; tribe Triticeae; tribe Aveneae such as oat; tribe Chloridinae such as *Eragrostis curvula*; and tribe Paniceae such as foxtail millet and crabgrass. These plants are also included in the plants on which field resistance to blast can be conferred.

As used herein, "suppression of Pi21 gene expression" includes suppression of gene transcription and suppression of translation to a protein. Moreover, it includes not only the complete arrest of DNA expression, but also reduction of expression.

One embodiment of "a DNA used to suppress Pi21 gene expression" is a DNA which encodes an antisense RNA complementary to the Pi21 gene. Using the temporal gene expression method, the antisense effect in a plant cell was demonstrated for the first time through the fact that an antisense RNA introduced by electroporation exhibited an antisense effect in a plant (Ecker and Davis, Proc. Natl. Acad. USA, 83: 5372, 1986). Thereafter, expression of antisense RNAs in tobacco and petunia have also been reported to reduce target gene expression (Krol et. al., Nature 333: 866, 1988). At present, it is established as a means to suppress gene expression in plants.

There are a number of factors involved in the action of antisense nucleic acids in suppressing target gene expression, as indicated as follows: inhibiting transcription initiation by forming triple strands; suppressing transcription by hybridizing with a site where RNA polymerase has formed a local open loop structure; inhibiting transcription by hybridizing with the RNA being synthesized; suppressing splicing by hybridizing with an intron-exon junction; suppressing splicing by hybridizing with the site of spliceosome formation; suppressing transfer from the nucleus to the cytoplasm by hybridizing with an mRNA; suppressing splicing by hybridizing with a poly(A) addition site or capping site; suppressing translation initiation by hybridizing with a translation initiation factor binding site; suppressing translation by hybridizing with a ribosome binding site near the initiation codon; preventing peptide chain elongation by hybridizing with an mRNA translation region or polysome binding site; and suppressing gene expression by hybridizing with a nucleic acid-protein interaction site. Antisense nucleic acids suppress target gene expression by inhibiting transcription, splicing, or translation process (Hirashima and Inoue, 1993, "Shin Seikagaku Jikken Kouza (New Biochemistry Experimentation Lectures) 2, Kakusan (Nucleic Acids) IV, Idenshi No Fukusei To Hatsugen (Replication and Expression of Genes)", The Japanese Biochemical Society Ed., Tokyo Kagaku Dojin, pp. 319-347).

The antisense sequences used in the present invention can suppress the expression of a target gene by any of the above actions. As one embodiment, an antisense sequence designed to be complementary to an untranslated region close to the 5' end of the mRNA of a gene will be effective in inhibiting translation of that gene. However, a sequence complementary to a coding region, or to a 3'-end untranslated region can also be used. In this way, DNAs comprising antisense sequences of a gene's translated regions as well untranslated regions are included in the antisense DNAs that can be used in the present invention. An antisense DNA to be used herein is ligated downstream of an appropriate promoter, and a sequence comprising a transcription termination signal is preferably ligated to the 3' side of the DNA.

Antisense DNAs can be prepared, for example, based on the DNA sequence of SEQ ID NO: 1, 2, 20, or 21 by using the phosphorothioate method (Stein, Nucleic Acids Res., 16: 3209-3221, 1988) and such. DNAs thus prepared can be transformed into a desired plant using known methods. Antisense DNA sequences are preferably sequences complementary to a transcription product of an endogenous gene of the plant to be transformed, but need not be perfectly complementary as long as they can effectively inhibit gene expression. The transcribed RNAs are preferably 90% or more (for example, 95%, 96%, 97%, 98%, 99% or more) complementary to the transcription products of the target genes. In order to effectively inhibit target gene expression using an antisense sequence, an antisense DNA should comprise at least 15 nucleotides or more, preferably 100 nucleotides or more, and even more preferably 500 nucleotides or more. Antisense DNAs to be used are generally less than 5 kb, and preferably less than 2.5 kb long.

Suppression of the endogenous Pi21 gene expression can also be carried out using DNAs encoding ribozymes. The term "ribozyme" refers to an RNA molecule having catalytic activity. Some ribozymes have many different activities. Among them, research on ribozymes as RNA-cleaving enzymes has enabled designing ribozymes to cleave RNAs at specific sites. Ribozymes include those of 400 nucleotides or more, such as M1RNA in RNaseP, or the group 1 intron type ribozymes. In contrast, there are also hammerhead-type or hairpin-type ribozymes that comprise an active domain of about 40 nucleotides (Koizumi, M. and Ohtsuka, E., 1990, Protein, Nucleic acid and Enzyme, 35: 2191-2200).

For example, the self-cleaving domain of a hammerhead type ribozyme cleaves at the 3' side of C15 in G13U14C15. Base pairing between U14 and A9 is important for ribozyme activity. It has been shown that cleavage can occur if A or U instead of C is at the 15th position (Koizumi, M. et al., 1988, FEBS Lett. 228: 228-230). If the substrate-binding site of the ribozyme is designed to be complementary to the RNA sequences adjacent to the target site, a restriction enzyme-like RNA-cleaving ribozyme can be created that recognizes the sequence UC, UU, or UA within the target RNA (Koizumi et al., 1988, FEBS Lett. 239: 285; Koizumi, M. and Ohtsuka, E., 1990, Protein, Nucleic acid and Enzyme, 35: 2191; Koizumi et al., 1989, Nucleic Acids Res. 17: 7059).

Hairpin type ribozymes are also useful for objectives of the present invention. A hairpin type ribozyme can be found, for example, in the minus strand of tobacco ringspot virus satellite RNA (Buzayan, Nature 323: 349, 1986). It has also been shown that this ribozyme can be designed to target-specifically cleave an RNA (Kikuchi and Sasaki, Nucleic Acids Res. 19: 6751, 1992; Kikuchi, H., Kagaku to Seibutsu (Chemistry and Biology) 30: 112, 1992).

In order to be transcribed in plant cells, a ribozyme designed to cleave a target is linked to a transcription termination sequence or a promoter such as the cauliflower mosaic virus 35S promoter. However, if extra sequences are added to the 5'- or the 3'-end of the transcribed RNA, the ribozyme activity can be lost. In this case, another cis-acting trimming ribozyme can be placed in the 5' or 3' side of the ribozyme portion to precisely trim only the ribozyme portion from the transcribed RNA comprising the ribozyme (Taira et al., Protein Eng. 3: 733, 1990; Dzianott and Bujarski, Proc. Natl. Acad. Sci. USA 86: 4823, 1989; Grosshans and Cech, Nucleic Acids Res. 19: 3875, 1991; Taira et al., Nucleic Acid Res. 19: 5125, 1991).

In addition, these structural units can be arranged in tandem to cleave multiple sites within a target gene, thus achieving greater effects (Yuyama et al., Biochem. Biophys. Res. Commun. 186: 1271, 1992). By using these kinds of ribozymes, the transcription products of the target genes of the present invention can be specifically cleaved, and the gene expression can be suppressed.

Suppression of endogenous gene expression can also be achieved by "co-suppression" resulting from transformation with a DNA comprising a sequence identical or similar to a target gene sequence. The term "co-suppression" refers to the phenomenon in which, when a gene comprising a sequence identical or similar to that of the target endogenous gene is introduced into plants by transformation, expression of both the introduced exogenous gene and the target endogenous gene is suppressed. The detailed mechanism of co-suppression is unknown, but it is frequently observed in plants (Curr. Biol., 7: R793, 1997; Curr. Biol. 6: 810, 1996).

For example, to obtain a plant in which the Pi21 gene is co-suppressed, plants of interest are transformed with a vector DNA constructed to express the Pi21 gene or a DNA comprising a similar sequence, and plants with a characteristic of a mutant Pi21, i.e., plants with field resistance to blast, are selected from the plants thus obtained. Genes to be used for co-suppression do not have to be completely identical to the target gene; however, they have sequence identity of at least 70% or more, preferably 80% or more, and more preferably 90% or more (for example, 95%, 96%, 97%, 98%, 99% or more).

In addition, suppression of endogenous gene expression in the present invention can also be achieved by transforming a plant with a gene comprising a characteristic that is dominant-negative to the target gene. A "gene comprising a dominant-negative characteristic" refers to a gene that, when expressed, has the function of eliminating or reducing the activity of an original endogenous wild-type gene of the plant.

Another embodiment of "a DNA used to suppress Pi21 gene expression" is a DNA which encodes a double-stranded RNA (dsRNA) complementary to a transcription product of an endogenous Pi21 gene. By introducing a dsRNA comprising a sequence identical or similar to a target gene sequence into a cell, a phenomenon called RNAi (RNA interference) can be caused, where expression of both the introduced foreign gene and the target endogenous gene are suppressed. When a dsRNA of about 40 to several hundred base pairs is introduced into a cell, an RNase III-like nuclease comprising a helicase domain, called Dicer, cuts out about 21 to 23 base pair portions from the 3'-terminus of the dsRNA in the presence of ATP, thereby producing an siRNA (short interference RNA). This siRNA binds to a specific protein to form a nuclease complex (RISC: RNA-induced silencing complex). This complex recognizes and binds to a sequence identical to the siRNA, and cuts the transcription product (mRNA) of the target gene at the central part of the siRNA with the RNaseIII-like enzymatic activity. Apart from this pathway, an antisense strand of siRNA binds to an mRNA to act as a primer of an RNA-dependent RNA polymerase (RsRP), thereby synthesizing a dsRNA. Another pathway is also considered in which this dsRNA serves again as a substrate of Dicer, produces a new siRNA, and amplifies its effect.

RNAi was first discovered in nematodes (Fire, A. et al., Potent and specific genetic interference by double-stranded RNA in *Caenorhabditis elegans*. Nature 391, 806-811, 1998). At present, it is observed not only in nematodes, but also in various organisms such as plants, *Nemathelminthes, Drosophila*, and protozoa (Fire, A. RNA-triggered gene silencing. Trends Genet. 15, 358-363 (1999); Sharp, P. A. RNA interference 2001. Genes Dev. 15, 485-490 (2001); Hammond, S. M., Caudy, A. A. & Hannon, G. J. Post-transcriptional gene silencing by double-stranded RNA. Nature Rev. Genet. 2, 110-119 (2001); Zamore, P. D. RNA interference: listening to the sound of silence. Nat Struct Biol. 8, 746-750 (2001)). In these organisms, it was confirmed that target gene expression was actually suppressed by externally introducing a dsRNA. Further, RNAi is now being used as a method for creating knockout organisms.

When RNAi was initially found, only a dsRNA of a certain length (40 bases) or more was thought to be effective. However, Tuschl et al. of Rockefeller University, United States, reported that by introducing a short dsRNA (siRNA) of about 21 base pairs into a cell, an RNAi effect was obtained in a mammalian cell without causing an antiviral reaction by PKR (Tuschl, Nature, 411, 494-498 (2001)). Thus, RNAi has suddenly attracted attention as a technique applicable to differentiated mammalian cells such as human cells.

The DNAs of the present invention comprise an antisense code DNA encoding an antisense RNA corresponding to any region of a transcription product (mRNA) of a target gene, and a sense code DNA encoding a sense RNA corresponding to any region of the mRNA. The above-mentioned antisense RNA and sense RNA can be expressed from the above-mentioned antisense code DNA and sense code DNA. A dsRNA can also be produced from these antisense RNA and sense RNA. A target sequence in the present invention is not particularly limited, as long as the Pi21 gene expression is suppressed by introducing into a cell a dsRNA comprising a sequence identical or similar to the target sequence. An example of the target sequence includes a sequence of 3'-untranslated region of the Pi21 gene. A sequence of 3'-untranslated region of the Pi21 gene is shown in SEQ ID NOs: 11 and 24.

An expression system of dsRNAs of the present invention is maintained as follows in a vector or the like: an antisense RNA and a sense RNA are expressed from the same vector; or an antisense RNA and a sense RNA are expressed from different vectors, respectively. For example, when expressing an antisense RNA and a sense RNA from the same vector, an antisense RNA expression cassette and sense RNA expression cassette are each constructed, in which a promoter like the pol III system that can express a short RNA is connected upstream of the antisense code DNA and sense code DNA, respectively, and these cassettes are then inserted into a vector in the same direction or in the opposite direction.

An expression system can also be constructed in which an antisense code DNA and a sense code DNA are arranged in opposite directions on different strands so that they face each other. This construct can carry one double-stranded DNA (siRNA code DNA) in which an antisense RNA-encoding strand and a sense RNA-encoding strand are paired, and promoters which are oppositely oriented on both sides so that the antisense RNA and the sense RNA can be expressed from each strand. In this case, in order to prevent addition of an excess sequence downstream of the sense RNA and the antisense RNA, a terminator is preferably placed at the 3'-terminus of each strand (the antisense RNA-encoding strand and the sense RNA-encoding strand). A sequence of four or more consecutive A (adenine) bases can be used for this terminator. Moreover, in this palindrome type expression system, the kinds of two promoters are preferably different to each other.

When expressing an antisense RNA and sense RNA from different vectors, for example, the following procedures are performed: An antisense RNA expression cassette and a sense RNA expression cassette are constructed, in each of which a promoter such as the pol III system that can express a short RNA, is connected upstream of the antisense code DNA or the sense code DNA; and then these cassettes are maintained in different vectors.

As for RNAi, an siRNA may be used as a dsRNA. The term "siRNA" means a double-stranded RNA including short strands that exhibit no toxicity within a cell, and is not limited to the full length of 21 to 23 base pairs reported by Tuschl et al. (ibid.); and is not particularly limited, as long as the length is in such a range that it exhibits no toxicity. For example, an siRNA can be 15 to 49 base pairs, preferably 15 to 35 base pairs, and still more preferably 21 to 30 base pairs in length. Alternatively, length of the final double-stranded RNA portion that results from transcription of an siRNA to be expressed, can be 15 to 49 base pairs, preferably 15 to 35 base pairs, and more preferably 21 to 30 base pairs, for example.

As a DNA of the present invention, such a construct that is produced by inserting a suitable sequence (an intron sequence is preferable) between the inverted repeats of a target sequence (Smith, N. A., et al. Nature, 407: 319, 2000; Wesley, S. V. et al. Plant J. 27: 581, 2001; Piccin, A. et al. Nucleic Acids Res. 29: E55, 2001) and yields a double-stranded RNA having a hairpin structure (self-complementary 'hairpin' RNA (hpRNA)), can also be used.

Although a DNA used for RNAi is not required to be completely the same as a target gene, it has a sequence identity of at least 70% or more, preferably 80% or more, still more preferably 90% or more (for example, 95%, 96%, 97%, 98%, 99% or more). The sequence identity can be determined by using the above-mentioned procedures.

The double-stranded RNA portions in dsRNAs, in which RNAs are paired, are not necessarily completely paired, but may comprise unpaired portions due to a mismatch (corresponding bases are not complementary), a bulge (there is no corresponding base on one strand) or the like. In the present invention, both bulges and mismatches may be included in double-stranded RNA regions where RNAs are paired with each other in dsRNAs.

The present invention also provides vectors and transformed cells comprising any one of the Pi21 gene, the pi21 gene, and DNAs that suppress Pi21 gene expression.

With regard to the above vectors, for example, when the host is *E. coli*, as long as the vector has an "ori" for amplification in *E. coli*, such that vectors are amplified and prepared in large quantities in *E. coli* (for example, JM109, DH5α, HB101, and XL1Blue) or such, and further has a selection gene for transformed *E. coli* (for example, a drug resistance gene that allows discrimination using a certain drug (ampicillin, tetracycline, kanamycin, or chloramphenicol)), the vectors are not particularly limited. The vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs. When using vectors to produce the Pi21 gene, the pi21 gene, and the DNAs that suppress Pi21 gene expression, expression vectors are particularly useful. When an expression vector is expressed in *E. coli*, for example, it should have the above characteristics in order to be amplified in *E. coli*. Additionally, when *E. coli* such as JM109, DH5α, HB101, or XL1-Blue are used as the host, the vector must have a promoter that allows efficient expression in *E. coli*, for example, a lacZ promoter (Ward et al. Nature 341:544-546, 1989; FASEB J. 6: 2422-2427, 1992), araB promoter (Better et al. Science 240:1041-1043, 1988), or T7 promoter. Other examples of the vectors include pGEX-5X-1 (Pharmacia), "QIAexpress system" (QIAGEN), pEGFP, and pET.

Furthermore, the vector may comprise a signal sequence for polypeptide secretion. When producing polypeptides into the periplasm of *E. coli*, the pelB signal sequence (Lei, S. P. et al. J. Bacteriol. 169:4379 (1987)) may be used as a signal sequence for polypeptide secretion. For example, calcium chloride methods or electroporation methods may be used to introduce the vector into a host cell.

In addition to *E. coli*, expression vectors derived from mammals (e.g., pcDNA3 (Invitrogen), pEGF-BOS (Nucleic Acids Res. 18(17): 5322 (1990)), pEF, and pCDM8), insect cells (e.g., "Bac-to-BAC baculovirus expression system" (GIBCO-BRL) and pBacPAK8), plants (e.g., pMH1 and pMH2), animal viruses (e.g., pHSV, pMV, and pAdexLcw), retroviruses (e.g., pZIPneo), yeasts (e.g., "Pichia Expression Kit" (Invitrogen), pNV11 and SP-Q01), and *Bacillus subtilis* (e.g., pPL608 and pKTH50) may also be used as vectors for producing the Pi21 gene, the pi21 gene, and the DNAs which suppress Pi21 gene expression.

For expression in animal cells such as CHO, COS, and NIH3T3 cells, the vector must have a promoter necessary for expression in such cells, for example, an SV40 promoter (Mulligan et al. Nature 277: 108 (1979)), MMLV-LTR promoter, EF1α promoter (Mizushima et al. Nucleic Acids Res. 18: 5322 (1990)), or CMV promoter. It is even more preferable that the vector comprises a gene for selecting transformants (for example, a drug-resistance gene enabling discrimination by a drug (such as neomycin and G418)). Examples of vectors with such characteristics include pMAM, pDR2, pBK-RSV, pBK-CMV, pOPRSV, and pOP13.

Introduction of a DNA of the present invention into a cell can be carried out by a method known to one skilled in the art, for example, by an electroporation method.

Further, the present invention provides transformed plant cells into which the DNA encoding the Pi21 protein or a DNA suppressing the Pi21 gene expression has been introduced; transformed plants derived from the cells; transformed plants which are progenies or clones of the transformed plants; and propagation materials of the transformed plants. Methods for producing the above-mentioned transformants and propagation materials are also provided.

The DNA encoding the Pi21 protein or DNAs suppressing Pi21 gene expression can be introduced into plant cells by the above methods.

In addition, regeneration of plants is also possible using methods known to those skilled in the art, according to the type of plant cell (Toki et al., Plant Physiol., 100: 1503-1507, 1995). In rice, for example, a number of techniques for producing transformed plants are already established, and are widely used in the technical field of the present invention. These methods include the method for introducing genes into protoplasts using polyethylene glycol and then regenerating plants (suitable for Indian varieties of rice) (Datta et al., In Gene Transfer To Plants. Potrykus, I. and Spangenberg, G. Eds., pp. 66-74, 1995), the method for introducing genes into protoplasts using electric pulse and then regenerating plants (suitable for Japanese varieties of rice) (Toki et al., Plant Physiol. 100: 1503-1507, 1992), the method for directly introducing genes into cells using the particle gun method and then regenerating plants (Christou et al., Bio/technology, 9: 957-962, 1991), and the method for introducing genes via an *Agrobacterium*, and then regenerating plants (Hiei et al., Plant J., 6: 271-282, 1994). These methods can be appropriately used in the present invention.

When using the above *Agrobacterium* method, the method of Nagel et al. (Microbiol. Lett. 67: 325, 1990) is used, for example. In this method, a recombinant vector is transformed into an *Agrobacterium*, and subsequently the transformed *Agrobacterium* is introduced into a cell by a known method such as the leaf disk method. The above-mentioned vector comprises an expression promoter so that, for example, the DNA encoding the Pi21 protein of the present invention or a DNA suppressing the Pi21 gene expression is expressed in a plant after introduction into the plant. Generally, DNA encoding the Pi21 protein of the present invention or a DNA suppressing the Pi21 gene expression is located downstream of the promoter, and a terminator is located further downstream of such a DNA. The recombinant vector used for this purpose is suitably selected by one skilled in the art, depending on the type of plant or method of introduction. The above-mentioned promoters include, for example, the CaMV35S derived from cauliflower mosaic virus and the ubiquitin promoter from corn (JP-A H2-79983).

Examples of the above-mentioned terminator can be a terminator derived from cauliflower mosaic virus and the terminator from the nopaline synthase gene; however, the promoter and terminator are not limited thereto, as long as they function in a plant.

The plants into which the DNA encoding the Pi21 protein of the present invention or a DNA suppressing the Pi21 gene expression is introduced, may be explants, or the DNA may be introduced into the cultured cells prepared from these plants. "Plant cells" in the present invention include, for example, plant cells of a leaf, root, stem, flower, and scutellum in a seed; calluses; and suspension-cultured cells.

In order to efficiently select the cells transformed by introducing the DNA encoding the Pi21 protein of the present invention or a DNA suppressing the Pi21 gene expression, the above-mentioned recombinant vector is introduced into the plant cells, preferably together with a suitable selection marker gene or a plasmid vector comprising a selection marker gene. The selection marker genes used for this purpose include, for example, the hygromycin phosphotransferase gene resistant to the antibiotic hygromycin, the neomycin phosphotransferase resistant to kanamycin or gentamycin, and the acetyltransferase gene resistant to the herbicide phosphinothricin.

The cells into which the recombinant vector has been introduced are placed on a known selection medium containing a suitable selection agent depending on the type of introduced selection marker gene, and then cultured. In this way, the transformed plant cultured cells can be obtained.

Next, plant bodies reproduced from the transformed cells are cultured in an acclimation medium. The acclimated, regenerated plant bodies are then grown under usual culture conditions to obtain plant bodies having field resistance to blast, from which seeds can be obtained once they mature and bear fruit.

The presence of the introduced foreign DNAs in the transformed plants that are regenerated and grown in this manner can be confirmed by the known PCR method or Southern hybridization method, or by analyzing the nucleotide sequences of the DNAs in plant bodies.

In this case, extraction of the DNAs from the transformed plants can be carried out according to the known method by J. Sambrook et al. (Molecular Cloning, the 2nd edition, Cold Spring Harbor Laboratory Press, 1989).

When analyzing the foreign genes which are present in the regenerated plant bodies and include the DNAs of the present invention, using the PCR method, an amplification reaction is carried out using as a template the DNAs extracted from the regenerated plant bodies as mentioned above. An amplification reaction can also be performed in a reaction mixture containing as primers synthesized oligonucleotides which comprise nucleotide sequences suitably selected according to the nucleotide sequences of the DNAs of the present invention or the DNAs modified according to the present invention. In the amplification reaction, denaturation, annealing, and extension reactions of DNAs can be repeated several tens of times to obtain amplified products of DNA fragments comprising the DNA sequences of the present invention. By subjecting the reaction mixture comprising the amplified products, for example, to agarose electrophoresis, the various kinds of amplified DNA fragments are fractionated, thereby enabling confirmation of whether a certain DNA fragment corresponds to a DNA of the present invention.

After obtaining a transformed plant in which a DNA encoding the Pi21 protein of the present invention or a DNA suppressing the Pi21 gene expression has been introduced into the chromosome, progenies can be obtained by sexual or asexual reproduction from the plant. Further, propagation materials (for example, seeds, fruits, panicles, tubers, tuberous roots, stocks, calluses, and protoplasts) can also be obtained from the plant or its progenies or clones, and these materials can be used to mass-produce the plants. The present invention comprises plant cells into which the DNA encoding the Pi21 protein or a DNA suppressing the Pi21 gene expression has been introduced; plants comprising the cells; progenies and clones of the plants; and propagation materials of the plants and their progenies and clones. Such plant cells, plants comprising the cells, progenies and clones of the plants, and propagation materials of the plants and their progenies and clones, can be used in methods for conferring plants with field resistance to blast.

The present invention further provides methods for conferring plants with field resistance to blast, comprising the step of expressing a DNA which suppresses Pi21 gene expression in cells of plant bodies. Field resistance to blast can be conferred on plants by introducing into plant cells vectors which comprise, in an expressible state, a DNA suppressing Pi21 gene expression, using the above-mentioned methods, and by regenerating plants using these cells.

As used herein, the term "'conferring' field resistance to blast" means not only to provide a blast field resistance capacity to plants having no blast field resistance capacity, but also to further increase blast field resistance capacity of plants which already have it.

In the present invention, plants in which Pi21 gene expression is suppressed and on which field resistance to blast is conferred, are not particularly limited; and such plants include, for example, the above-mentioned plants.

The present invention also provides proteins encoded by the Pi21 gene of the present invention, methods for producing the proteins, and antibodies which bind to the proteins.

Recombinant proteins are typically prepared by inserting DNAs encoding proteins of the present invention into appropriate expression vectors, introducing the vectors into appropriate cells, culturing the transformed cells, and purifying the expressed proteins. Recombinant proteins can be expressed as fusion proteins with other proteins to make purification easier, for example, as fusion proteins with maltose-binding protein using *Escherichia coli* as a host (New England Biolabs, USA, vector pMAL series), as fusion proteins with glutathione S-transferase (GST) (Amersham Pharmacia Biotech, vector pGEX series), or tagged with histidine (Novagen, pET series). The host cells are not particularly limited, so long as the cell is suitable for expressing the recombinant proteins. It is possible to use, for example, yeast, various plant or animal cells, insect cells or such in addition to the above-described *E. coli*. Vectors can be introduced into host cells by a variety of methods known to those skilled in the art. For example, introduction methods using calcium ions can be used for introduction into *E. coli* (Mandel, M. & Higa, A. Journal of Molecular Biology, Vol.53, 158-162 (1970); Hanahan, D. Journal of Molecular Biology, Vol.166, 557-580 (1983)). Recombinant proteins expressed in the host cells can be purified and recovered from the host cells or the culture supernatant thereof by known methods in the art. When recombinant proteins are expressed as fusion proteins with the aforementioned maltose-binding protein or such, affinity purification can be carried out easily.

The obtained recombinant proteins can be used to prepare antibodies which bind to the proteins. Polyclonal antibodies can be obtained as follows, for example: Small animals such as rabbits are immunized with the Pi21 protein a recombinant protein expressed as a fusion protein with GST in microorganisms such as *E. coli.*, or its partial peptide to obtain sera. The antibodies are prepared by purifying the sera using, for example, ammonium sulfate precipitation, a protein A or protein G column, DEAE ion exchange chromatography, or an affinity column coupled with the Pi21 protein or a synthetic peptide. Monoclonal antibodies can be prepared as follows: small animals such as mice are immunized with the Pi21 protein or its partial peptide; the spleen is harvested from the mice and ground to separate cells; the cells and mouse myeloma cells are fused using a reagent such as polyethylene glycol; and from among the fused cells (hybridomas) thus obtained, clones which produce antibodies binding to the Pi21 protein are selected. Subsequently, the obtained hybridomas are transplanted into the abdominal cavity of mice, ascites are collected from the mice to prepare monoclonal antibodies, for example, by purifying using ammonium sulfate precipitation, a protein A or protein G column, DEAE ion exchange chromatography, an affinity column coupled with the Pi21 protein or a synthetic peptide. The antibodies thus obtained can be used for purification, detection and the like of the proteins of the present invention. The present invention comprises antibodies which bind to the proteins of the present invention.

The present invention provides oligonucleotides comprising at least 15 nucleotides which are complementary to the pi21 gene, a DNA comprising the Pi21 gene, or the complementary strand thereof.

A "complementary strand" herein refers to one strand relative to the other strand in a double-stranded nucleic acid comprising base pairs of A:T (U for RNA) and G:C. The term "complementary" means not only that a sequence is completely complementary in a region of at least 15 consecutive nucleotides, but also that a sequence has a homology of at least 70%, preferably at least 80%, more preferably 90%, still more preferably 95% or more in the nucleotide sequence. Any algorithm known to one skilled in the art may be used for determining homology.

The oligonucleotides of the present invention can be used as probes or primers for detection and amplification of DNAs comprising the nucleotide sequence of SEQ ID NO: 1, 2, 4, 5, 20, or 21. Moreover, the oligonucleotides of the present invention can be used in the form of a DNA array substrate.

When such an oligonucleotide is used as a primer, the length is usually 15 by to 100 bp, and preferably 17 by to 30 bp. The primer is not particularly limited, as long as it can amplify at least a portion of a DNA of the present invention or its complementary strand. When used as a primer, its 3' side region is made to be complementary, and a restriction enzyme recognition sequence, a tag or the like can be added to its 5' side.

When the above-mentioned oligonucleotide is used as a probe, any oligonucleotide may be used without particular limitation, as long as it can specifically hybridize at least a portion of a DNA comprising the nucleotide sequence of SEQ ID NO: 1, 2, 4, 5, 20, or 21 or its complementary strand. The probe may be a synthetic oligonucleotide, and usually has a length of at least 15 bp or more.

When an oligonucleotide of the present invention is used as a probe, it is preferably labeled as appropriate. Labeling methods include the following, for example: a method in which the 5' end of an oligonucleotide is phosphorylated by $^{32}P$ using T4 polynucleotide kinase; and a method (the random primed method or the like) in which substrate bases labeled with an isotope such as $^{32}P$, a fluorescent dye, or biotin are incorporated into an oligonucleotide, using a DNA polymerase such as Klenow enzyme and using random hexamer oligonucleotides and the like as a primer.

The oligonucleotides of the present invention can be produced, for example, with a commercially available oligonucleotide synthesizer. The probes can also be produced as double-stranded DNA fragments obtained by restriction enzyme treatment or the like.

Further, the present invention provides uses of DNAs suppressing Pi21 gene expression and vectors comprising the DNAs. That is, the present invention relates to agents for increasing field resistance to blast in plants, which comprise any one of a DNA suppressing Pi21 gene expression and a vector comprising the DNA as an active ingredient. Moreover, the present invention relates to uses of DNAs suppressing Pi21 gene expression and vectors comprising the DNAs, for preparing agents for increasing field resistance to blast in plants.

The agents for increasing field resistance to blast in plants of the present invention may include, for example, sterilized water, physiological saline, vegetable oil, surfactants, lipids, solubilizing agents, buffers, and preservatives, if needed, in addition to active ingredients, i.e., the oligonucleotides.

The present invention also provides molecular markers linked to the susceptibility gene Pi21 or the resistance gene pi21.

The term "molecular marker" in the present invention means a DNA region which is genetically linked to the Pi21 gene or the pi21 gene and distinguishable from other DNA regions.

In general, when the map distance between a gene and a molecular marker expressed with cM unit is shorter, the molecular marker is located closer to the gene. Such a molecular marker is highly useful because it will be inherited together with the gene. pi21 was shown to be located between the marker "Pa102484" and the marker "P702D3_#12" (FIG. 2*c*). Accordingly, in the methods of the present invention, among the molecular markers described in FIG. 2*c*, the above two markers and the markers located between the two markers ("P702D03_#38", "P702D03_#79", "P702D03_#80") are preferable. Among them, ""P702D03_#79" is an especially preferable marker and can be exemplified as the DNA of SEQ ID NO: 7 or 23 (linked to the susceptibility gene Pi21), or SEQ ID NO: 10 (linked to the resistance gene pi21).

The molecular markers of the present invention include Sequence Tagged Site (STS) markers. The term "STS marker" refers to a DNA region which can be used to judge the presence or absence of polymorphism of a sequence tagged site (STS) on a DNA, and the term "STS" refers to a specific sequence site at a particular position of a DNA. The polymorphism of STS can be detected as the presence or absence of bands or the difference in band position, by amplifying a DNA region comprising a specific sequence site with a nucleic acid amplification method such as the PCR method, and then subjecting the amplification products to agarose or polyacrylamide gel electrophoresis.

When a STS marker is used as a molecular marker of the present invention, the identification methods of the present invention can be carried out as follows, for example. First, DNA samples are prepared by a well-known method from a test rice plant and from a rice plant having field resistance to blast. Next, a nucleic acid amplification reaction (for example, the PCR method) is carried out by using the prepared DNAs as a template and using primer DNAs. The sizes of the amplified DNA fragments are compared between the test rice plant and a marker linked to the gene for field resistance to blast (for example, the marker of SEQ ID NO: 10) by electrophoresis or the like, and when they show the same genotype, it is judged that the test plant has field resistance to blast.

One skilled in the art can appropriately design optimal primer DNAs used for the identification methods of the present invention, considering the sequence information on various molecular markers. Usually, the above-mentioned primers are a primer set consisting of a pair of primers which are designed to sandwich a nucleotide sequence that specifically exists in rice and is linked to the Pi21 gene or the pi21 gene, for amplifying the nucleotide sequence.

Specifically, primer sets for STS markers can include the following, for example:

```
(a) a primer set consisting of primers
                                        (SEQ ID NO: 8)
5'-AGA AGG TGG AGT ACG ACG TGA AGA-3'
and (SEQ ID NO: 9)
5'-AGT TTA GTG AGC CTC TCC ACG ATT A-3', (b) a primer set consisting of primers
                                       (SEQ ID NO: 16)
5'-GTA CGA CGT GAA GAA CAA CAG G-3'
and (SEQ ID NO: 17)
5'-GCT TGG GCT TGC AGT CC-3',
and (c) a primer set consisting of primers
                                       (SEQ ID NO: 26)
5'-GAT CCT CAT CGT CGA CGT CTG GC-3'
and (SEQ ID NO: 27)
5'-AGG GTA CGG CAC CAG CTT G-3'.
```

The presence of field resistance to blast in the test rice plant can be judged by comparing the information characterized by the DNA sequences amplified using these primer sets with the molecular markers of the present invention Besides the above-mentioned primers, one skilled in the art can produce primer sets having a similar function utilizing the nucleotide sequence of SEQ ID NO: 1, 4, or 20. The primers of the present invention also comprise such primers.

One skilled in the art can produce PCR primers of the present invention using, for example, an automatic oligonucleotide synthesizer. One skilled in the art can also perform the methods of the present invention by using a known polymorphism detection method such as the below-mentioned PCR-SSCP method using the above PCR primers, or the like.

When molecular markers of the present invention are located in exons of a genomic DNA, it is also possible to utilize RT-PCR using mRNAs as a template. By using the Taqman (a quantitative PCR detection) system (Roche), the presence or absence of amplification products can be detected by fluorescence. Since this system does not need electrophoresis, it enables one to carry out the identification methods of the present invention in a short time.

The present invention further provides methods for judging that the test plants have field resistance to blast when the molecular weight or the nucleotide sequence is consistent with that of the pi21 gene, which methods comprise the following steps (a) to (c):

(a) preparing DNA samples from test plants;

(b) amplifying the region of Pi21 gene or pi21 gene from the DNA samples; and (c) comparing the molecular weight or the nucleotide sequence of the amplified DNA fragments with that of the pi21 gene.

One skilled in the art can prepare (extract) the above-mentioned DNA samples of the present invention by known methods. Preferable preparation methods include, for example, a method for extracting DNAs using the CTAB method.

The DNA samples used in the identification methods of the present invention are not particularly limited; however, genomic DNAs extracted from a test plant, rice, are usually used. The source for the genomic DNA extraction is not particularly limited, and the DNAs can be extracted from any tissue of rice. They can be extracted, for example, from a panicle, leaf, root, stem, seed, endosperm portion, bran, or embryo.

In the methods of the present invention for identifying field resistance to blast in plants, a nucleic acid amplification reaction (for example, the PCR method) is subsequently carried out by using the prepared DNAs as a template and using primer DNAs. The amplified DNA fragments are cleaved by restriction enzymes, and the sizes of the cleaved DNA fragments are compared between the test plants and plants having field resistance to blast, by electrophoresis or the like. When the molecular weight or the nucleotide sequence is consistent with that of the compared plants, the test plants are judged to have field resistance to blast. "Plants having field resistance to blast" include *Owarihatamochi* described in Examples, but are not limited thereto.

In the methods of the present invention for judging that test plants have field resistance to blast, the term "consistent with" means that the molecular weight or the nucleotide sequence of both genes of an allele is consistent with that of a plant having field resistance to blast, or that the deduced amino acid sequence of such genes is consistent with that of the plant. Accordingly, when the molecular weight, nucleotide sequence, or deduced amino acid sequence of one gene of an allele differs from that of a plant having field resistance to blast, but that of the other gene of the allele is the same as that of the plant, such a case is not included in the term "consistent with".

The above-mentioned electrophoresis analysis may be conducted according to a conventional method. For example, electrophoresis is carried out by applying voltage in an agarose or polyacrylamide gel, and the separated DNA pattern is analyzed.

The present invention also provides methods for judging that the test plants have field resistance to blast when the mobility on the gel is consistent with that of the pi21 gene, which methods comprise the following steps (a) to (d):
(a) preparing DNA samples from test plants;
(b) amplifying the region of the Pi21 gene or the pi21 gene from the DNA samples;
(c) separating the amplified double-stranded DNAs on a non-denaturating gel; and
(d) comparing the mobility of the separated double-stranded DNAs on the gel with that of the pi21 gene.

The present invention further provides methods for judging that the test plants have field resistance to blast when the mobility on the gel is consistent with that of the pi21 gene, which methods comprise the following steps (a) to (e):
(a) preparing DNA samples from test plants;
(b) amplifying the region of the Pi21 gene or the pi21 gene from the DNA samples;
(c) dissociating the amplified DNAs into single-stranded DNAs;
(d) separating the dissociated single-stranded DNAs on a non-denaturating gel; and
(e) comparing the mobility of the separated single-stranded DNAs on the gel with that of the pi21 gene.

The above methods include the PCR-SSCP (single-strand conformation polymorphism) method ("Cloning and polymerase chain reaction-single-strand conformation polymorphism analysis of anonymous Alu repeats on chromosome 11." Genomics 1992, Jan. 1, 12(1): 139-146; "Detection of p53 gene mutations in human brain tumors by single-strand conformation polymorphism analysis of polymerase chain reaction products." Oncogene 1991, Aug. 1; 6(8): 1313-1318; "Multiple fluorescence-based PCR-SSCP analysis with post-labeling." PCR Methods Appl. 1995, Apr. 1; 4(5): 275-282).

This method is particularly preferable for screening many DNA samples, since it has advantages such as comparative simplicity of operation and a small amount of required test sample. The principle of the method is as follows. A single-stranded DNA dissociated from a double-stranded DNA fragment forms a unique higher conformation, depending on the respective nucleotide sequence. After electrophoresis on a polyacrylamide gel without a denaturant, complementary single-stranded DNAs having the same chain length shift to different positions in accordance with the difference of the respective higher conformations. The conformation of a single-stranded DNA changes even by a substitution of one base, which change results in a different mobility on polyacrylamide gel electrophoresis. Accordingly, the presence of a mutation in a DNA fragment due to a point mutation, deletion, insertion and such can be detected by detecting the changes in the mobility.

More specifically, a region comprising a target site of the Pi21 gene or the pi21 gene is first amplified by the PCR method or the like. Preferably, a region to be amplified is about 100 by to 600 by in length. In amplifying gene fragments by PCR, DNA fragments to be synthesized can be labeled by using primers labeled with an isotope such as $^{32}P$, a fluorescent dye, biotin and so on, or by adding substrate nucleotides labeled with an isotope such as $^{32}P$, a fluorescent dye, biotin and so on, to the PCR reaction solution. Alternatively, the synthesized DNA fragments can be labeled after the PCR reaction by adding substrate nucleotides labeled with an isotope such as $^{32}P$, a fluorescent dye, biotin and so on using the Klenow enzyme and such. The DNA fragments thus obtained are electrophoresed in the form of a double strand on a polyacrylamide gel without a denaturant such as urea. Alternatively, such DNA fragments may be denatured by heating and the like, and then subjected to electrophoresis on a polyacrylamide gel without a denaturant such as urea. The conditions for separating DNA fragments can be ameliorated by adding appropriate amounts (about 5% to 10%) of glycerol to the polyacrylamide gel. Further, although the electrophoresis conditions varies depending on the properties of respective DNA fragments, it is usually carried out at room temperature (20° C. to 25° C.). When a preferable separation cannot be achieved, a temperature to achieve the optimal mobility is selected from temperatures between 4° C. and 30° C. After the electrophoresis, the mobility of the DNA fragments is detected by autoradiography using X-ray films, a scanner for detecting fluorescence and the like, to analyze the result. When bands with different mobility are detected, the presence of a mutation can be confirmed by directly excising the bands from the gel, amplifying them again by PCR, and directly sequencing the amplified fragments. Even when labeled DNAs are not used, the bands can also be detected by staining the gel after electrophoresis with ethidium bromide, silver and such.

The present invention further provides methods for judging that the test plants have field resistance to blast when the sizes of the detected DNA fragments are consistent with that of the pi21 gene, which methods comprise the following steps (a) to (e):
(a) preparing DNA samples from test plants;
(b) amplifying the region of the Pi21 gene or the pi21 gene from the DNA samples;
(c) cleaving the prepared DNA samples with restriction enzymes;
(d) separating the DNA fragments according to their sizes; and
(e) comparing the sizes of the detected DNA fragments with that of the pi21 gene.

The above methods include the RFLP method using Restriction Fragment Length Polymorphism (RFLP) and the PCR-RFLP method. Restriction enzymes are generally used as enzymes to cleave DNAs. Specifically, when a nucleotide addition or deletion exists in the recognition site of a restriction enzyme, or when a nucleotide insertion or deletion exists in a DNA fragment generated by a restriction enzyme treatment, the sizes of the fragments generated after the restriction enzyme treatment differ between plants susceptible to blast and plants having field resistance to blast. The portion comprising such a mutation site is amplified by the PCR method, and then treated with each restriction enzyme to detect the polymorphic site as a difference in the mobility of bands by electrophoresis. Alternatively, a polymorphic site can be detected by treating chromosomal DNAs with such a restriction enzyme, subjecting the fragments to electrophoresis, and then carrying out Southern blotting with a probe DNA. The restriction enzymes to be used can be appropriately selected in accordance with respective mutation sites. In this method, Southern blotting can be performed not only on genomic DNAs but also on cDNAs which are synthesized by a reverse transcriptase from RNAs prepared from subjects and then directly cleaved with restriction enzymes. Alternatively, a part or whole of the Pi21 gene or the pi21 gene can be amplified by PCR using such cDNAs as a template, and cleaved with restriction enzymes, and then the difference in mobility can be examined.

The present invention provides methods for judging that the test plants have field resistance to blast when the mobility on the gel is consistent with that of the pi21 gene, which methods comprise the following steps (a) to (d):
(a) preparing DNA samples from test plants;
(b) amplifying the region of the Pi21 gene or the pi21 gene from the DNA samples;
(c) separating the amplified DNAs on a gel with a gradually increasing concentration of a DNA denaturant; and
(d) comparing the mobility of the separated DNAs on the gel with that of the pi21 gene.

The denaturant gradient gel electrophoresis method (DGGE method) can be exemplified as one of such methods. A region comprising a target site of the Pi21 gene or the pi21 gene is amplified by the PCR method and the like using a primer of the present invention and such; the resulting products are electrophoresed on a polyacrylamide gel with a gradually increasing concentration of a denaturant such as urea; and the result is compared with that of a healthy subject. A polymorphism can be identified by detecting the difference in mobility of the DNA fragments, since the mobility rate of fragments with mutations decreases drastically as the DNA fragments become single-stranded DNAs at lower denaturant concentration points.

In addition to the above-mentioned methods, the Allele Specific Oligonucleotide (ASO) hybridization method can be used. An oligonucleotide comprising a nucleotide sequence where a polymorphism is predicted to exist, is prepared, and is subjected to hybridization with a DNA sample. When a polymorphic nucleotide different from the oligonucleotide exists in the sample DNA used for hybridization, the efficiency of hybridization is reduced. The reduction of the hybridization efficiency can be detected by the Southern blotting method; methods which utilize specific fluorescent reagents that have a characteristic to quench by intercalation into a gap of a hybrid; and the like.

Furthermore, the detection may be conducted by the ribonuclease A mismatch truncation method. Specifically, a region comprising a target site of the Pi21 gene or the pi21 gene is amplified by the PCR method and the like, and the amplified products are hybridized with labeled RNAs which are prepared from healthy-type cDNAs and such incorporated into a plasmid vector and the like. Since the hybrid forms a single strand conformation in a portion comprising a nucleotide different from the healthy-type, a polymorphism can be detected by cleaving this portion with ribonuclease A and then performing autoradiography and the like.

In the present invention, the term "test plant" is not particularly limited, but includes all plants that can be infected with the blast fungus. A preferable example is rice. Every variety of rice can be used without any particular restriction, such as Indica or Japonica rice varieties, and Indica-Japonica hybrid varieties/lines, wild rice, or cultivar-wild rice hybrid or crossbred varieties.

The present invention also provides methods for judging field resistance to blast in rice by using as an indicator a molecular marker which is linked to the pi21 gene and comprises at least the DNA of SEQ ID NO: 7, 10, or 23. Preferable molecular markers of the present invention include "P702D03_#38", "P702D03_#79", and "P702D03_#80", as mentioned above. Among them, ""P702D03_#79" is an especially preferable marker, and it may be the DNA of SEQ ID NO: 7 or 23 (linked to the susceptibility gene Pi21) or SEQ ID NO: 10 (linked to the resistance gene pi21), for example. The identification methods of the present invention use as an indicator at least "P702D03_#79" among these molecular markers. Therefore, in the identification methods of the present invention, "P702D03_#79" may be used alone or in combination with other markers. The combinations of "P702D03_#79" with other markers include the combination with "P702D03_#38", combination with "P702D03_ #80", and combinations with any other markers.

In the identification methods of the present invention, field resistance to blast in test rice plants can be judged specifically and efficiently by examining whether they comprise a molecular marker linked to the pi21 gene. In the judging methods of the present invention, when a desired rice plant to be judged for having field resistance to blast or not comprises the nucleotide sequence of SEQ ID NO: 10, the test rice plant is judged to have field resistance to blast. When the test rice plant does not comprise the nucleotide sequence of SEQ ID NO: 10 (when it comprises the nucleotide sequence of SEQ ID NO: 7 or 23), it is judged to be susceptible to blast.

Molecular markers in test rice plants can be compared with those of the present invention not only for the DNA sequences of molecular markers, but also for the information characterized by the DNA sequences. The information characterized by the DNA sequences of molecular markers includes information about the molecular weight of the molecular markers and about the presence or absence of a mutation site and polymorphic site comprised in the molecular markers. One skilled in the art can identify polymorphic sites (deletion sites and single base-substitution sites) by comparing the nucleotide sequence of SEQ ID NO: 10 with that of SEQ ID NO: 7 or 23 using known methods. The judging methods of the present invention can also be performed by detecting such information on the presence or absence of a mutation site or polymorphic site comprised in molecular markers.

The above information on the presence or absence of a mutation site or polymorphic site can be detected by using primers which can amplify a region comprising a mutation site or polymorphic site, or by using a probe (for example, the DNA comprising the whole or a part of the nucleotide sequence of SEQ ID NO: 18, 19, or 25) which can hybridize to a mutation site or polymorphic site, as well as by directly determining the sequences.

By using the judging methods of the present invention, it becomes possible to select at an early stage plants (for example, rice) to be identified as having field resistance to blast. Specifically, the present invention provides methods for selecting plants having field resistance to blast, which comprise the following steps (a) and (b):

(a) producing varieties in which plants (for example, rice) having field resistance to blast have been crossed with plants (for example, rice) having arbitrary functions;
(b) judging whether the plants obtained in step (a) have field resistance to blast by the methods herein described for judging whether test plants have field resistance to blast.

The term "plant" is not particularly limited in the present invention, but preferably refers to rice. Specific examples of rice are as mentioned above.

By using the selection methods of the present invention, it becomes possible to select at an early stage plants (for example, rice) to be identified as having field resistance to blast. The present invention also provides such methods for selecting at an early stage plants to be identified as having field resistance to blast. As used herein, the term "early stage" refers to, for example, the state before heading of rice, and preferably the state immediately after germination. By using the selection methods of the present invention, it becomes possible to breed varieties having field resistance to blast in a shorter period than before.

The present invention relates to methods of screening for agents to prevent or ameliorate blast in plants. The first embodiment of the screening methods of the present invention includes methods of screening for agents to prevent or ameliorate blast in plants, which comprise the following steps (a) to (c):

(a) contacting test compounds with a Pi21 gene transcription product;
(b) detecting the binding of the test compounds to the Pi21 gene transcription product; and
(c) selecting test compounds that bind to the Pi21 gene transcription product.

In the first embodiment, test compounds are first contacted with the Pi21 gene transcription product. "Pi21 gene transcription product" in the screening methods of the present invention includes not only the Pi21 gene transcription product, but also the translation product translated from the transcription product.

The "test compounds" in the methods of the present invention are not particularly limited, and include, for example, single compounds such as natural compounds, organic compounds, inorganic compounds, proteins, and peptides; as well as compound libraries, expression products of gene libraries, cell extracts, cell culture supernatants, products of fermentation microorganisms, marine organism extracts, plant extracts, prokaryotic cell extracts, unicellular eukaryote extracts, and animal cell extracts. If needed, the above test compounds can be appropriately labeled before use. Labels include, for example, radiolabels and fluorescent labels.

In the present invention, "contacting" is carried out as follows. For example, if the Pi21 gene transcription product is in a purified state, the contact can be carried out by adding test compounds to the purified preparation. If the transcription product is in the state expressed in cells, or in the state expressed in cell extracts, the contact can be carried out by adding test compounds to the cell cultures or to the cell extracts, respectively. The cells in the present invention are not particularly limited, but cells derived from plants including rice are preferable. When the test compounds are proteins, the contact can also be carried out, for example, by introducing vectors comprising the DNAs encoding the proteins into cells expressing the Pi21 gene, or by adding the vectors to cell extracts in which the Pi21 gene is expressed. Further, for example, two hybrid methods using yeast or animal cells can be utilized.

In the first embodiment, the binding between the above-mentioned Pi21 gene transcription product and test compounds is subsequently detected. Detection or measurement of the binding between proteins can be carried out by using, for example, labels attached to the proteins. The types of labels include, fluorescent labels and radiolabels, for example. The binding can also be measured by known methods such as the yeast two hybrid method and the method using BIACORE. In the present methods, the test compounds bound to the above-mentioned biosynthesis enzyme are then selected. Among the selected test compounds, agents for preventing or ameliorating blast in plants are included. The selected test compounds may be used as test compounds in the following screenings.

In addition, the second embodiment of the screening methods of the present invention provides methods of screening for agents to prevent or ameliorate blast in plants, which comprise the following steps (a) to (c):

(a) contacting test compounds with cells collected from plants;
(b) measuring the expression level of thePi21 gene transcription product; and
(c) selecting the test compounds that decrease the expression level of the transcription product as compared to when the test compounds are not contacted with the cells.

In the second embodiment, test compounds are first contacted with cells collected from plants. As used herein, the term "cells collected from a plant" may be an arbitrary plant clearly having a blast susceptibility gene. The terms "test compound" and "contacting" refer to the same as mentioned above.

In the second embodiment, the expression level of the "Pi21 protein" is subsequently measured. The expression level of the Pi21 protein can be measured by methods known to one skilled in the art. For example, mRNA encoding the Pi21 protein is extracted according to a conventional method, and the transcription level of the Pi21 gene can be measured by performing the Northern hybridization method or the RT-PCR method using this mRNA as a template. Further, the expression level of the Pi21 protein can be measured using DNA array techniques.

The translation level of the gene can also be measured by collecting fractions comprising the Pi21 protein in accordance with a usual method, and detecting the expression of the Pi21 protein by electrophoresis such as SDS-PAGE. The translation level of the gene can also be measured by performing the Western blotting method using an antibody against the Pi21 protein to detect the expression of the Pi21 protein.

The antibodies used for detection of the Pi21 protein are not particularly limited, as long as they can detect the Pi21 protein. Both monoclonal antibodies and polyclonal antibodies can be used, for example. The antibodies can be prepared as mentioned above, by methods known to one skilled in the art.

In the second embodiment, next, when the expression level of the Pi21 protein decreases compared to when the test compounds are not contacted, the test compounds are selected as agents to prevent or ameliorate blast in plants.

The third embodiment of the screening methods of the present invention provides methods of screening for agents to prevent or ameliorate blast in plants, which comprise the following steps (a) to (d):

(a) providing cells or cell extracts comprising DNAs in which a reporter gene is operably linked downstream of the promoter region of the Pi21 gene;
(b) contacting test compounds with cells or the cell extracts;
(c) measuring the expression level of the reporter gene in the cells or the cell extracts; and
(d) selecting test compounds that decrease the expression level of the reporter gene as compared to when the test compounds are not contacted.

In the third embodiment, cells or cell extracts comprising DNAs in which a reporter gene is operably linked downstream of the promoter region of the Pi21 gene, are first provided.

In the third embodiment, the term "operably linked" means that the promoter region of the Pi21 gene and a reporter gene are connected to each other so that the reporter gene expression can be induced by binding of a transcription factor to the promoter region of the Pi21 gene. Therefore, the term "operably linked" also inlcudes such cases where a reporter gene is connected to another gene and produces a fused protein with another gene product, as long as expression of the fused protein is induced by binding of a transcription factor to the promoter region of the Pi21 gene.

The reporter gene is not particularly limited, so long as its expression can be detected. For example, reporter genes generally used by those skilled in the art include the CAT gene, lacZ gene, luciferase gene, β-glucuronidase gene (GUS), and GFP gene.

In the third embodiment, the above-mentioned cells or cell extracts are subsequently contacted with the test compounds. Then, the expression level of the reporter gene in the cells or the cell extracts is measured. The terms "test compound" and "contacting" refer to the same as mentioned above.

The expression level of the reporter gene can be determined using methods known to those skilled in the art, according to the type of reporter gene. For example, when using the CAT gene as the reporter gene, the CAT gene expression level can be determined by measuring the acetylation of chloramphenicol, caused by the CAT gene product. When the lacZ gene is used as the reporter gene, its expression level can be determined by analyzing the colouring of a dye compound due to the catalytic action of the gene expression product. The expression level of the luciferase gene as a reporter can be determined by measuring the fluorescence of a fluorescent compound, caused by the catalytic action of the luciferase gene expression product. The expression level of the β-glucuronidase (GUS) gene can be determined by analyzing the coloring of 5-bromo-4-chloro-3-indolyl-β-glucuronide (X-Gluc) or the luminescence of Glucuron (ICN), caused by the catalytic action of the GUS gene expression product. The expression level of the GFP gene can be determined by measuring fluorescence due to the GFP protein.

Next in the third embodiment, if the expression level of the above-mentioned genes decrease compared to when the test compounds are not contacted, the test compounds are selected as agents to prevent or ameliorate blast in plants.

The fourth embodiment of the screening methods of the present invention provides methods of screening for agents to prevent or ameliorate blast in plants, which comprise the following steps (a) to (c):
(a) regenerating transformed plants from transformed plant cells into which the Pi21 gene has been introduced;
(b) contacting the blast fungus and test compounds with the transformed plants; and
(c) selecting test compounds that suppress blast in the transformed plants as compared to when the test compounds are not contacted.

In the fourth embodiment, transformed plants are first regenerated from transformed plant cells comprising the Pi21 gene. The transformed plants can be regenerated as mentioned above, by a method known to one skilled in the art.

In the fourth embodiment, next, the blast fungus and test compounds are contacted with the transformed plants regenerated in step (a). The terms "blast fungus" and "test compound" are the same as mentioned above. An example of "contacting" is a method for directly spraying a test compound on a plant using a sprayer. However, "contacting" in the fourth embodiment is not limited thereto, but includes any method, as long as plants and test compounds can physically contact. The contact of the present invention may be performed by contacting test compounds with transformed plants infected with the blast fungus, or by infecting with the blast fungus transformed plants which have contacted with test compounds.

In the fourth embodiment, next, test compounds that suppress blast in transformed plants as compared to when test compounds are not contacted, are selected. Whether blast is suppressed or not can be determined by using as an indicator a phenotype of the transformed plants. The phenotypes of the transformed plants are not particularly limited, but include discoloring and necrotizing of an entire part of a plant, or a portion of it. Moreover, suppression of blast in the transformed plants includes not only complete suppression but also partial suppression.

The present invention also relates to kits for use in the above-described screening methods. Such kits can comprise materials used at the detection step and/or measurement step in the above-described screening methods. For example, such materials can include probes, primers, antibodies, and stain solutions, which are necessary for measuring Pi21 gene expression level. In addition, the kits may comprise distilled water, salts, buffer solutions, protein stabilizers, preservatives and the like.

All prior art references cited in the present specification are incorporated herein by reference.

EXAMPLES

Hereinafter, the present invention will be specifically described with reference to Examples, but it is not construed as being limited thereto.

Example 1

Genetic Mapping

A detailed linkage analysis of the pi21 region was conducted using a large-scale segregating population indispensable for map-based cloning. As the population for linkage analyses, 72 samples of the BC1F2 population were used. This BC1F2 population was obtained by continuously backcrossing the paddy rice variety *Nipponbare* or *Aichi Asahi* (FIG. 1) comprising the susceptibility allele Pi21 that does not suppress blotch progression with the Japanese upland rice variety *Owarihatamochi* comprising the resistance allele pi21 that suppresses blotch progression. As a result of linkage analysis with RFLP markers, it was found that the pi21 gene locus is located between the RFLP markers G271 and G317 (FIG. 2A).

Figure 2:
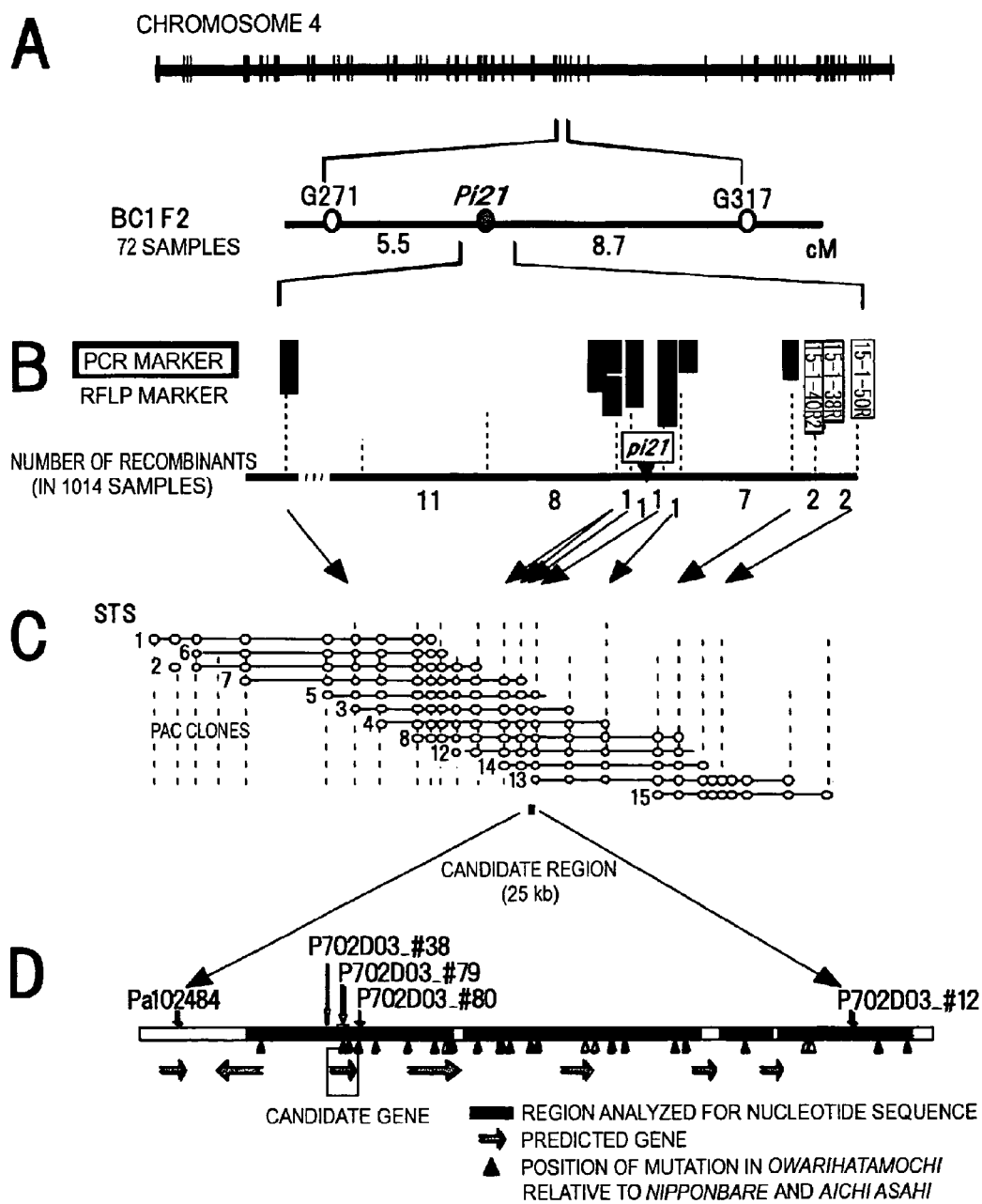
FIG. 2 shows detailed linkage maps of the pi21 gene region, and an alignment map of genomic clones.

In order to create a more accurate genetic map of the pi21 region, a total of 1014 samples including the above-mentioned crossbred 229 samples and 643 samples of the progeny BC1F4 population were used to select 27 samples with chromosomal recombination near the pi21 locus, by using the RFLP markers RA3591 and 13S1 located on both sides of the pi21 locus (FIG. 2B). Furthermore, a search was carried out using 2703 samples of F2 population, which was obtained by crossing a line having the genetic background of Japanese paddy rice variety and the susceptibility allele from the Indian paddy rice variety *Kasalath* with a line having the resistance allele from *Owarihatamochi*. 24 samples with chromosome recombination near the pi21 locus were selected using the PCR markers 14T1 and 4S1 located on both sides of the pi21 locus. Furthermore, using those samples, a detailed linkage map was created utilizing the DNA markers produced in the following procedures.

Example 2

Alignment of P1-derived Artificial Chromosome (PAC) Clones in the pi21 Gene Region Using the alignment map of *Nipponbare* PAC clones produced in the rice genome research program, PAC clones comprising the DNA markers RA3591 and C975 nucleotide sequences positioned near the pi21 gene locus were identified (FIG. 2C). Furthermore, terminal fragments of the identified PAC clones P479G02, P415D09, P473G08, P703E11, P434F09, P702D03, P419B08, P472G09, and P502G01 were isolated by the cassette method, and the identified PAC clones were aligned. As a result, it was found that the PAC clones P032D02, P678A02, P405D12, P689F04, P479G02, P415D09, P473G08, P703E11, P434F09, and P702D03 comprise the pi21 gene region (FIG. 2C).

Example 3

Narrowing the Candidate Region of the pi21 Gene

Terminal fragments of the PAC clones aligned in the pi21 region were cloned, and the obtained clones are used as new RFLP markers or CAPS markers to create a detailed genetic map. As a result, it was found that the pi21 gene locus exists in the genomic region sandwiched between the SSCP marker Pa102484 and the SNP marker P702D3_#12. Accordingly, it was revealed that the pi21 gene locus is located in the genomic region of about 25 kb sandwiched by the two markers (FIG. 2D).

Example 4

Identification of the Candidate Gene Region by Nucleotide Sequence Analysis

The nucleotide sequence of the PAC clone P702D03 considered to comprise the pi21 gene was determined, and the nucleotide sequence of 25 kb candidate genomic region in the resistant variety *Owarihatamochi* and the susceptible varieties *Aichi Asahi* and *Kasalath* were analyzed. The nucleotide sequence was analyzed by using the DNA fragments which were amplified from the above-mentioned three varieties with primers designed utilizing the sequence of the candidate region in *Nipponbare* and by using the dye-terminator method. The candidate region was further narrowed using the nucleotide polymorphism information in the candidate gene region identified by linkage analysis. As a result, the pi21 gene was shown to co-segregate with the STS marker P702D03_#79 (primers: 5'-AGA AGG TGG AGT ACG ACG TGA AGA-3' (SEQ ID NO: 8) and AGT TTA GTG AGC CTC TCC ACG ATT A-3' (SEQ ID NO: 9)), and one recombinant was detected between the SNP markers P702D03_#38 (primers: TTT TCC TGA GAA ATT TGT AAA GA-3' (SEQ ID NO: 12) and CGT CGA CGA TGA GGA TCT-3' (SEQ ID NO: 13)) and P702D03_#80 (primers: 5'-CTC CCA ATG TGT TTA GCA TC-3'(SEQ ID NO: 14) and 5'-CAA CCA TAT GTC CCT AAG GAT-3' (SEQ ID NO: 15)), respectively. These results showed that the pi21 gene is located in the genomic region of about 1.8 kb sandwiched between the SNP markers P702D03_#38 and P702D03_#80 (FIG. 2D)

The nucleotide sequence of the isolated Pi21 gene derived from rice (*Oryza sativa* L, varieties *Aichi Asahi* and *Nipponbare*) is shown in SEQ ID NO: 1, the nucleotide sequence of its cDNA is shown in SEQ ID NO: 2, and the amino acid sequence of the protein ("the Pi21 protein") encoded by the cDNA is shown in SEQ ID NO: 3. In addition, the nucleotide sequence of the Pi21 gene derived from *Kasalath*, corresponding to the Pi21 gene of *Aichi Asahi* and *Nipponbare*, is shown in SEQ ID NO: 20, the nucleotide sequence of its cDNA is shown in SEQ ID NO: 21, and the amino acid sequence of the protein (""the Pi21 protein") encoded by the cDNA is shown in SEQ ID NO: 22.

Example 5

Nucleotide Sequence Analysis of the pi21 Candidate Gene

Figure 3:
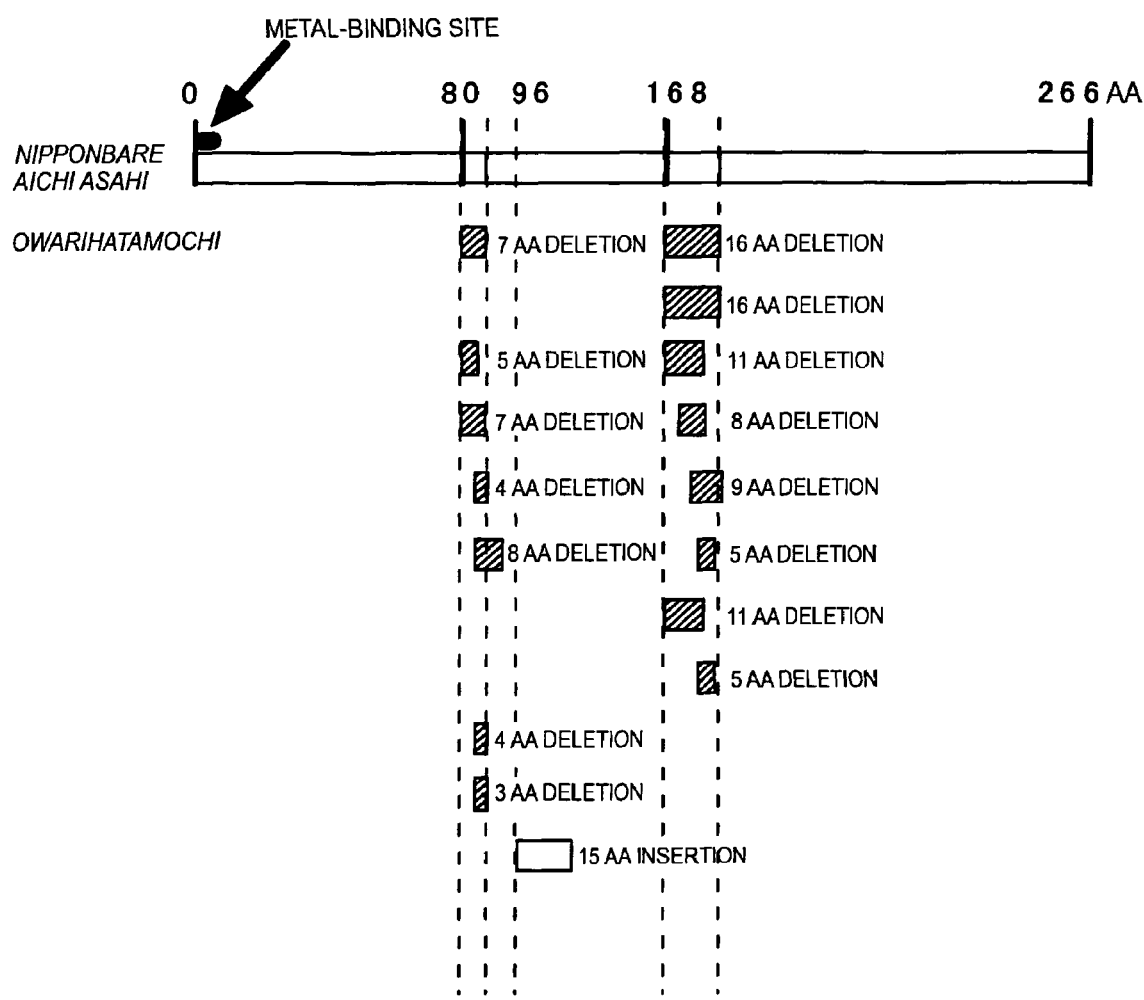
FIG. 3 shows a structure of a pi21 candidate gene, and a comparison between genomic nucleotide sequences of *Nipponbare* and *Aichi Asahi* and that of *Owarihatamochi*.

When a gene prediction and similarity search were carried out for the sequence of the 1.8 kb candidate genomic region of the variety *Nipponbare*, full-length cDNA clones of *Nipponbare* (AK106153, AK070581, and AK072320) were discovered. However, no similar genes were present in *Arabidopsis* or the like, and thus the function of the gene could not be predicted from homology. Nevertheless, a metal-binding site at a position about 10 amino acids away from the predicted translation initiation site in this gene brings to mind a gene reported in *Arabidopsis* (Hirayama et al., 1999 Cell) with the function of a chaperone which carries a metal in the ethylene signaling system. Since sensibility to ethylene in the near-isogenic line AA-pi21 is actually changed compared to *Aichi Asahi*, the site may have a similar function. Primers which can amplify the corresponding part were designed using the already obtained nucleotide sequence information of *Nipponbare*, and the nucleotide sequences of the genomic PCR and RT-PCR products of the susceptible varieties *Nipponbare* and *Aichi Asahi* were compared with those of the resistant variety *Owarihatamochi*. As a result, DNA mutations were found at two sites in the exon region of the gene in the resistant variety compared to the susceptible varieties. In the resistant variety, deletions of 7 amino acids and 16 amino acids were found relative to the susceptible varieties, and these mutations were thought to be associated with blotch progression in blast that had infected (FIG. 3).

The nucleotide sequence of the isolated pi21 gene is shown in SEQ ID NO: 4, the nucleotide sequence of its cDNA is shown in SEQ ID NO: 5, and the amino acid sequence of the protein encoded by the cDNA ("the pi21 protein") is shown in SEQ ID NO: 6.

Example 6

Identification of the Function of the Candidate Gene by Transformation (1) Introduction of the Susceptibility Gene into AA-pi21

Figure 4:
FIG. 4 shows photographs indicating blotches that appeared on the transformants of the resistant line AApi21 into which the Pi21 gene from *Nipponbare* was introduced. A: The vector alone was introduced. B: One copy of the Pi21 gene was introduced. C: Three or more copies of the Pi21 gene were introduced.
Figure 4:
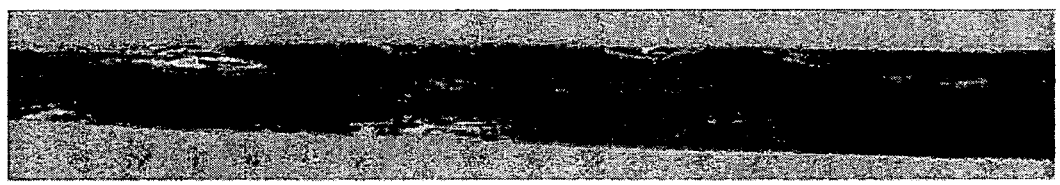
Figure 4:
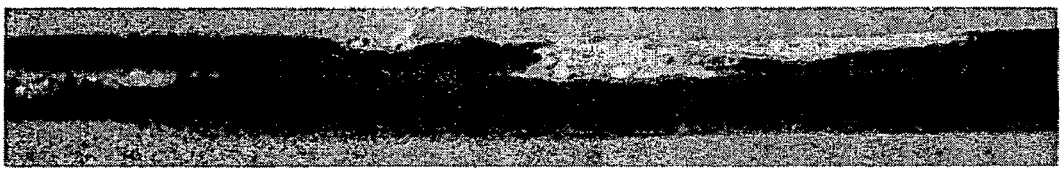

An XbaI 4.7 kb fragment of the genomic region including 5' upstream predicted promoter region of the susceptible variety *Nipponbare*, identified as a candidate of the pi21 gene, was incorporated into the vector pPZP2H-lac that can be transformed through *Agrobacterium*. Transformation was carried out by the method of Toki (Plant Mol. Biol. Rep. 15: 16-21, 1997) using a vector into which this fragment had been introduced and a vector alone. As the line to be transformed, the pi21 near-isogenic line AA-pi21 was used. 36 hygromycin-resistant organisms were obtained from the vector into which the XbaI 4.7 kb fragment had been introduced, and 12 hygromycin-resistant organisms were obtained from the vector alone. Whether the introduced region was incorporated or not, was investigated by the PCR method using primers (sense strand: 5'-GTA CGA CGT GAA GAA CAA CAG G-3' (SEQ ID NO: 16)) and (antisense strand: 5'-GCT TGG GCT TGC AGT CC 3' (SEQ ID NO: 17)) that were specific to the candidate gene. As a result, it was found that the candidate gene was incorporated into all the transformants. These organisms were grown in an isolated greenhouse, and the blast fungus (race 007) was inoculated into the inbred line progenies. As a result, in the organisms into which the vector alone was introduced and the T1 organisms into which the introduced gene was not delivered due to segregation, blotch progression caused by blast was suppressed as shown in the near-isogenic line AA-pi21, compared to the susceptible variety *Aichi Asahi*. In contrast, in the T1 organisms into which the candidate gene had been introduced, blotches progressed more extensively (FIG. 4). Especially, the degree of sensibility was increased in the lines having a high copy number of the introduced gene.

(2) Introduction of the Resistance Gene to a Susceptible Variety

On the other hand, the XbaI 4.7 kb fragment of the resistant variety *Owarihatamochi* was incorporated into the vector in the same way, and the susceptible variety *Aichi Asahi* was transformed. 56 Hygromycin-resistant organisms were obtained from the vector into which the XbaI 4.7 kb fragment had been introduced, and 24 hygromycin-resistant organisms were obtained from the vector alone. Similarly to (1), whether the introduced region was incorporated or not was investigated by the PCR method, and it was found that the candidate gene was incorporated into all the transformants. These organisms were grown in an isolated greenhouse in the same way as (1), and the blast fungus (race 007) was inoculated into the inbred line progenies. As a result, in all of the organisms into which the vector alone had been introduced, T1 organisms to which the introduced gene was not delivered, and T1 organisms into which the candidate gene had been introduced, blast progression was observed to the same degree as that in the susceptible variety *Aichi Asahi*.

(3) Identification of the Function of the Candidate Gene

From the above results, it was found that the candidate gene region from *Nipponbare* (XbaI 4.7 kb) has the function of promoting blotch formation in the near-isogenic line AA-pi21, and thus the candidate gene was judged to be the Pi21 gene.

Example 7

Mutations of the Candidate Gene in Rice

Mutations of the candidate gene were searched using 79 rice varieties in the world. As a result, in addition to the mutation types found in *Nipponbare*, *Aichi Asahi*, and *Owarihatamochi*, ten types of mutations having insertions and/or deletions in the exon region were found. These mutations are mainly defined by the presence or absence and the size of an insertion/deletion at the two deletion sites found in *Owarihatamochi* compared to *Nipponbare* and *Aichi Asahi*. Because of the similarity to the metal molecule chaperone proposed in the ethylene signaling system of *Arabidopsis thaliana*, this region having no homology with known genes is expected to bind to another molecule. Thus, the mutations in this region may delicately control the signaling efficiency and bring about functional alterations.

From the above results, the candidate gene narrowed down by the map-based cloning method was found to be the pi21 gene which suppresses blotch progression in rice blast disease. This achievement is the first case to prove the biological function of a quantitative resistance in a plant. The expression of the pi21 or the Pi21 gene was investigated by RT-PCR analysis, and each gene was found to be constitutively expressed in all the tissues of the aerial part. Therefore, it is expected that these genes play a fundamental role in the growth of plants. Since change of the copy number leads to phenotype changes, alteration of the expression level and the tissues where the genes are expressed by promoters can be an important factor for functional modification. That is, it may be possible to efficiently ameliorate disease resistance that plants originally have, by utilizing the isolated pi21 gene or other alleles found in the species.

Industrail Applicability

The characteristics of the Pi21 gene are especially suitable for producing varieties having field resistance to blast in plants. Until now, in order to confer plants with field resistance to blast, it was necessary to cross a variety that originally has field resistance and inferior characteristics with a variety that does not have field resistance but has many superior characteristics, and to select from among their progenies, plants having excellent field resistance as well as other excellent characteristics. However, the precise evaluation of field resistance needs a lot of effort. Moreover, when the exact position on the chromosome of the gene that confers this resistance is unclear, it is difficult to select this gene efficiently and accurately and to introduce it into a variety with a high practical use. In fact, this had not succeeded until now.

The present invention provides the chromosomal position and the structure of the gene involved in field resistance. Thus it became possible to efficiently confer plants with field resistance. It also became possible to breed varieties having resistance and highly practical characteristics by changing the tissue specificity of expression and the expression level of the gene participating in field resistance. Accordingly, the genes of the present invention are useful for realizing very practical and highly safe agriculture. Moreover, plants produced by the methods of the present invention are expected, for example, to stably give a high yield when it comes to useful agricultural plants, and also gain a new aesthetic value when it comes to ornamental plants.

The invention claimed is:

1. A method for determining whether a test plant has field resistance to blast, said method comprising the following steps:
   (a) preparing a DNA sample from the test plant;
   (b) amplifying a portion of the DNA sample, wherein the portion is selected from the group consisting of:
      (i) a DNA that encodes a protein comprising the amino acid sequence of SEQ ID NO: 3 or 22;
      (ii) a DNA comprising the coding region of the nucleotide sequence of SEQ ID NO: 1, 2, 20, or 21;
      (iii) a DNA encoding a protein which comprises an amino acid sequence 90% or more identity to the amino acid sequence of SEQ ID NO: 3 or 22, and which has the function of a protein comprising the amino acid sequence of SEQ ID NO: 3 or 22;
      (iv) a DNA that encodes a protein comprising the amino acid sequence of SEQ ID NO: 6;
      (v) a DNA comprising the coding region of the nucleotide sequence of SEQ ID NO: 4 or 5; and
      (vi) a DNA encoding a protein which comprises an amino acid sequence with 90% or more identity to the amino acid sequence of SEQ ID NO: 6, and which has the function of a protein comprising the amino acid sequence of SEQ ID NO: 6; and (c) comparing the amplified DNA with the DNA of (iv) or (v) to determine whether the test plant has field resistance to blast.

2. The method of claim 1, further comprising the steps of:
(d) separating the amplified double-stranded DNA on a non-denaturating gel;
(e) comparing the mobility of the separated double-stranded DNA on the gel with the mobility of the DNA of (iv) or (v) to determine whether the test plant has field resistance to blast.

3. The method of claim 1, further comprising the steps of:
(d) dissociating the amplified DNA into single-stranded DNAs;
(e) separating the dissociated single-stranded DNAs on a non-denaturating gel;
(f) comparing the mobility of the separated single-stranded DNAs on the gel with the mobility of the DNA of (iv) or (v) to determine whether the test plant has field resistance to blast.

4. The method of claim 1, further comprising the steps of:
(d) separating the amplified DNA on a gel with a gradually increasing concentration of a DNA denaturant; and
(e) comparing the mobility of the separated DNA on the gel, with the mobility of the DNA of (iv) or (v) to determine whether the test plant has field resistance to blast.

5. The method of claim 1, wherein the test plant is produced by crossing a plant having field resistance to blast with a plant having an arbitrary function.

6. A method for determining whether a test rice plant has field resistance to blast, said method comprising the following steps:
(a) determining the genotype of a molecular marker of the test rice plant, wherein the molecular marker is linked to a DNA of selected from the group consisting of:
(i) a DNA that encodes a protein comprising the amino acid sequence of SEQ ID NO: 3 or 22;
(ii) a DNA comprising the coding region of the nucleotide sequence of SEQ ID NO: 1, 2, 20, or 21;
(iii) a DNA encoding a protein which comprises an amino acid sequence 90% or more identity to the amino acid sequence of SEQ ID NO: 3 or 22, and which has function of a protein comprising the amino acid sequence of SEQ ID NO: 3 or 22;
(iv) a DNA that encodes a protein comprising the amino acid sequence of SEQ ID NO: 6;
(v) a DNA comprising the coding region of the nucleotide sequence of SEQ ID NO: 4 or 5; and
(vi) a DNA encoding a protein which comprises an amino acid sequence with 90% or more identity to the amino acid sequence of SEQ ID NO: 6, and which has the function of a protein comprising the amino acid sequence of SEQ ID NO: 6; and
(b) comparing the genotype of the molecular marker of the test plant to the genotype of the molecular marker of a rice plant having field resistance to blast to determine whether the test rice plant has field resistance to blast.

7. The method of claim 6, wherein the molecular marker comprises the DNA of SEQ ID NO: 10.

8. The method of claim 6, wherein the test plant is produced by crossing a rice plant having field resistance to blast with a rice plant having an arbitrary function.

9. The method of claim 2, wherein the test plant is produced by crossing a plant having field resistance to blast with a plant having an arbitrary function.

10. The method of claim 3, wherein the test plant is produced by crossing a plant having field resistance to blast with a plant having an arbitrary function.

11. The method of claim 4, wherein the test plant is produced by crossing a plant having field resistance to blast with a plant having an arbitrary function.

12. The method of claim 7, wherein the test plant is produced by crossing a rice plant having field resistance to blast with a rice plant having an arbitrary function.

13. The method of claim 1, further comprising the step of:
(d) comparing the molecular weight or nucleotide sequence of the amplified DNA to the molecular weight or nucleotide sequence of the DNA of (iv) or (v) to determine whether the test plant has field resistance to blast.

14. The method of claim 1, further comprising the step of selecting a plant having field resistance to blast.

* * * * *

UNITED STATES PATENT AND TRADEMARK OFFICE
CERTIFICATE OF CORRECTION

PATENT NO.      : 8,148,601 B2
APPLICATION NO. : 12/881685
DATED           : April 3, 2012
INVENTOR(S)     : Shuichi Fukuoka et al.

It is certified that error appears in the above-identified patent and that said Letters Patent is hereby corrected as shown below:

In the claims:

At column 61, claim number 6, line number 35, should read -- a DNA selected from the group consisting of: --

Signed and Sealed this
Fifth Day of June, 2012

David J. Kappos
*Director of the United States Patent and Trademark Office*